(12) United States Patent
Suzuki et al.

(10) Patent No.: US 11,076,815 B2
(45) Date of Patent: Aug. 3, 2021

(54) X-RAY CT APPARATUS

(71) Applicant: Hitachi, Ltd., Tokyo (JP)

(72) Inventors: Tsuyoshi Suzuki, Tokyo (JP); Ryouta Kohara, Tokyo (JP)

(73) Assignee: HITACHI, LTD., Tokyo (JP)

( * ) Notice: Subject to any disclaimer, the term of this patent is extended or adjusted under 35 U.S.C. 154(b) by 41 days.

(21) Appl. No.: 16/614,516

(22) PCT Filed: Mar. 23, 2018

(86) PCT No.: PCT/JP2018/011735
§ 371 (c)(1),
(2) Date: Nov. 18, 2019

(87) PCT Pub. No.: WO2018/235370
PCT Pub. Date: Dec. 27, 2018

(65) Prior Publication Data
US 2020/0178910 A1    Jun. 11, 2020

(30) Foreign Application Priority Data

Jun. 21, 2017   (JP) .............................. JP2017-121258

(51) Int. Cl.
*G06T 11/00*    (2006.01)
*A61B 5/055*    (2006.01)
(Continued)

(52) U.S. Cl.
CPC ............ *A61B 6/032* (2013.01); *A61B 6/4452* (2013.01); *A61B 6/5205* (2013.01); *A61B 6/541* (2013.01); *A61B 6/56* (2013.01)

(58) Field of Classification Search
CPC ......... G06T 1/20; G06T 5/001; G06T 11/008; G06T 15/005; G06T 7/0012;
(Continued)

(56) References Cited

U.S. PATENT DOCUMENTS

| 5,383,231 A | 1/1995 | Yamagishi |
|---|---|---|
| 2007/0165769 A1 | 7/2007 | Goto |

(Continued)

FOREIGN PATENT DOCUMENTS

| JP | 2003-079613 A | 3/2003 |
|---|---|---|
| JP | 2009-101086 A | 5/2009 |

(Continued)

OTHER PUBLICATIONS

International Search Report with English translation and Written Opinion issued in corresponding application No. PCT/JP2018/011735 dated Jun. 26, 2018.

*Primary Examiner* — Don K Wong
(74) *Attorney, Agent, or Firm* — Foley & Lardner LLP

(57) ABSTRACT

When image reconstruction by retrospective scanning is performed, the cache hit ratio is lowered due to transfer of not-used projection data to a cache memory. Accordingly, a processor generates rearranged projection data in which a first plurality of segments are extracted from original projection data written in a memory for saving original projection data 205, and stores the generated rearranged projection data into a main memory 212. The processor generates second view weights in which first view weights are made to correspond with the rearranged projection data (209). The rearranged projection data stored in the main memory 212 is previously transferred to the cache memory 213. The processor generates first tomographic image data with the rearranged projection data and the second view weights (214).

14 Claims, 18 Drawing Sheets

(51) Int. Cl.
*A61B 6/03* (2006.01)
*A61B 6/00* (2006.01)

(58) Field of Classification Search
CPC ......... G06T 2207/10072; G06T 11/005; G06T 7/10; G06T 11/006; A61B 5/055; A61B 6/032; A61B 6/56; A61B 6/541; A61B 6/4452; A61B 6/5205
See application file for complete search history.

(56) References Cited

U.S. PATENT DOCUMENTS

2007/0189436 A1    8/2007  Goto
2009/0110139 A1    4/2009  Noshi
2016/0267688 A1*  9/2016  Sulatycke ............. G06T 11/008

FOREIGN PATENT DOCUMENTS

WO    WO-2005/072613 A1    8/2005
WO    WO-2005/122901 A1    12/2005

* cited by examiner

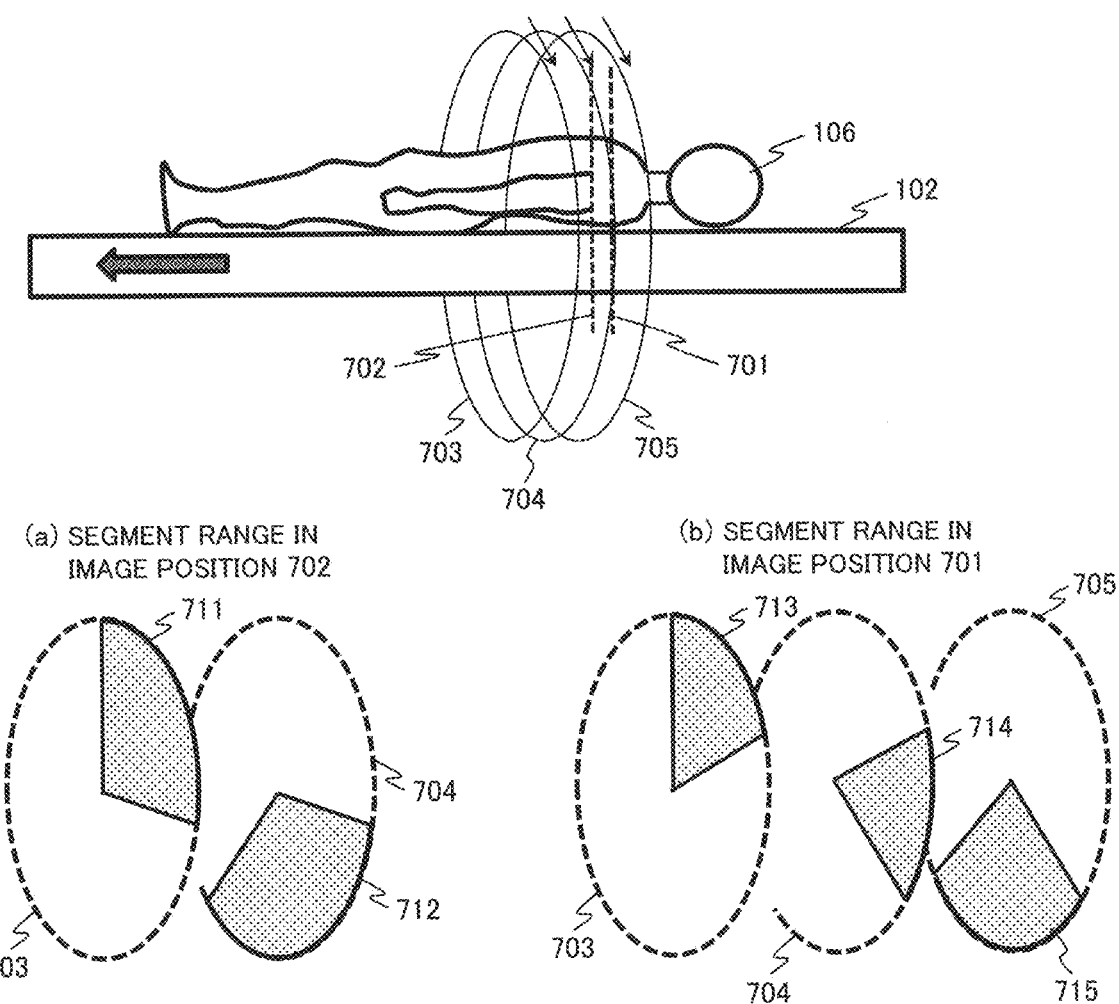

X-RAY CT APPARATUS

TECHNICAL FIELD

The present invention relates to an X-ray CT (Computed Tomography) apparatus, and more particularly, to an image processing technique of reconstructing a tomographic image from X-ray transmission data.

BACKGROUND ART

With respect to a part having a constant-period movement such as a heart, when a tomographic image is generated without consideration of the movement of the part, the tomographic image includes a motion artifact.

Patent literature 1 discloses obtaining a tomographic image of a heart during the diastolic period by inputting continuous projection data obtained by performing helical scanning and electrocardiographic waveform, converting the electrocardiographic waveform in a table position so as to reconstruct a tomographic image with projection data between R-waves as the diastolic period of the heart, and performing reconstruction by using the table position converted from the electrocardiographic waveform and the continuous projection data.

CITATION LIST

Patent Literature

PTL 1: Japanese Patent Application Laid-Open No. 2003-79613

SUMMARY OF INVENTION

Technical Problem

However, in the method disclosed in the patent literature 1, the continuous projection data also includes data not used in reverse projection. When the projection data which is not used is moved from a main memory to a cache memory, data used in the reverse projection is removed from the cache memory with the projection data not used in the reverse projection. This leads to reduction of the cache hit ratio, and eventually to delay of image processing.

The present invention has an object to provide an X-ray CT apparatus in which the cache hit ratio upon reverse projection of projection data is improved.

Solution to Problem

An X-ray CT apparatus includes: an X-ray tube; an X-ray detector, oppositely provided to the X-ray tube, that detects an X-ray generated with the X-ray tube and transmitted through a subject; a main memory that stores projection data generated from spatial distribution of the transmission X-ray detected with the X-ray detector; a cache memory to which the projection data is previously transferred from the main memory; and a processor that, when the projection data used in reverse projection processing has been transferred to the cache memory, performs the reverse projection processing, with the projection data stored in the cache memory, and generates tomographic image data of the subject. When a first plurality of segments are set based on an image position with respect to original projection data of continuous views from the X-ray detector, and first tomographic image data is generated by reverse-projecting projection data of the first plurality of segments in accordance with first view weights set by the first plurality of segments, the processor generates rearranged projection data in which the first plurality of segments are extracted from the original projection data, and stores the generated rearranged projection data into the main memory. The processor generates second view weights, in which the first view weights are made to correspond with the rearranged projection data. The rearranged projection data stored in the main memory is previously transferred to the cache memory. The processor generates the first tomographic image data with the rearranged projection data and the second view weights.

Advantageous Effects of Invention

According to the present invention, it is possible to provide an X-ray CT apparatus in which the cache hit ratio upon reverse projection of projection data is improved.

BRIEF DESCRIPTION OF DRAWINGS

FIG. 18 is a diagram explaining segment reconstruction.

DESCRIPTION OF EMBODIMENTS

Figure 1:
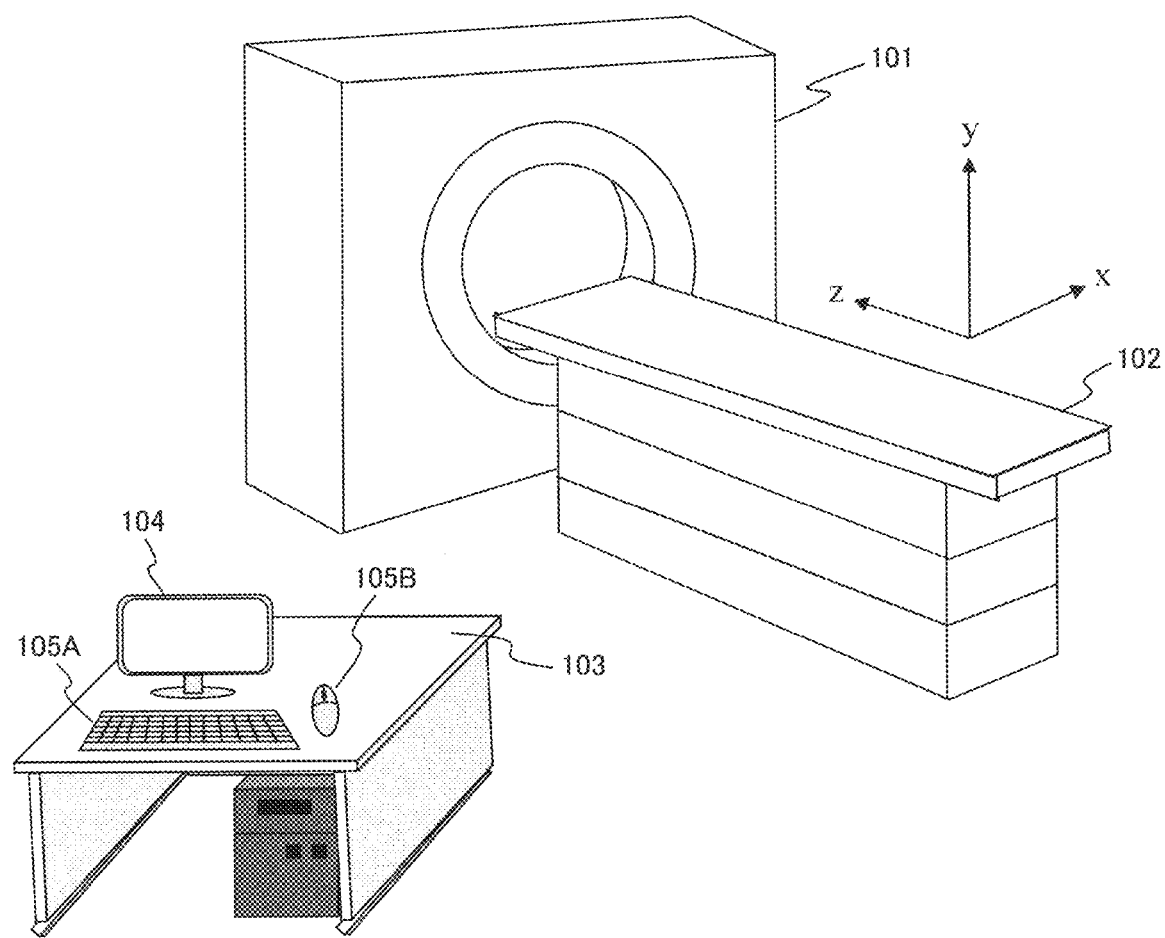
FIG. 1 is a diagram showing an outer appearance of an X-ray CT apparatus.
Figure 2:
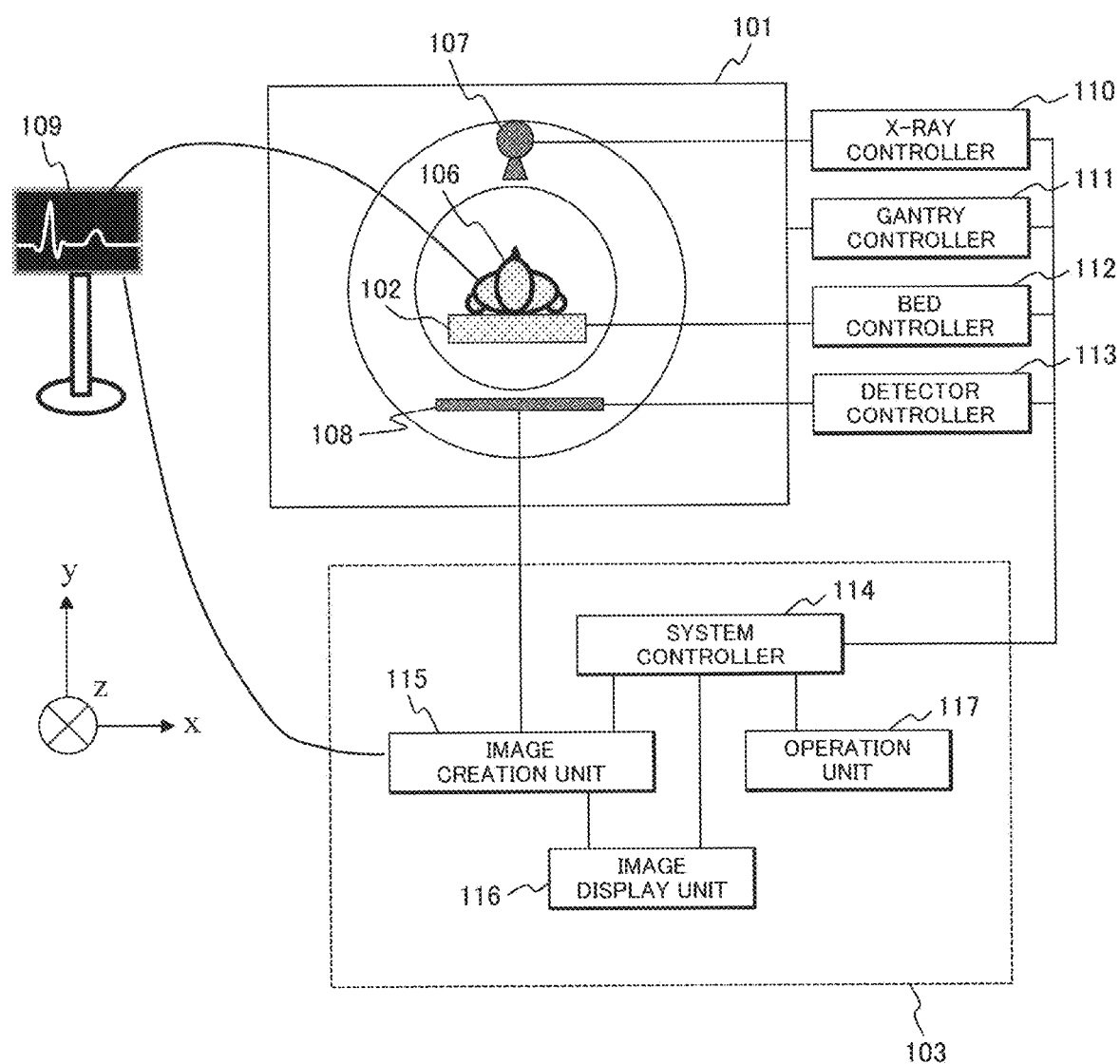
FIG. 2 is a block diagram of the X-ray CT apparatus.

Hereinbelow, an X-ray CT apparatus according to examples of the present invention will be described by using the attached drawings. FIG. 1 shows an outer appearance of the X-ray CT apparatus. FIG. 2 shows a block diagram of the X-ray CT apparatus. The X-ray CT apparatus is provided with a scanner 101 to perform X-ray image sensing on a subject on a bed 102, and a console 103 to control the X-ray image sensing with the scanner 101.

As shown in FIG. 2, the scanner 101 is provided with an X-ray tube 107, the bed 102, an X-ray detector 108, an X-ray controller 110, a gantry controller 111, a bed controller 112, and a detector controller 113. The X-ray tube 107 is a device which irradiates a subject 106 placed on the bed 102 with an X-ray. The bed 102 is a device on which the subject 106 is placed. The X-ray detector 108 is a device which is positioned on an opposite side to the X-ray tube 107 with a central part of the scanner 101 where the subject 106 is positioned, and which detects the X-ray transmitted through the subject 106 upon image sensing, thus measures the spatial distribution of the transmission X-ray. A large number of X-ray detection elements are two-dimensionally arrayed in the X-ray detector 108.

The X-ray controller 110 is a device which controls an electric current and the voltage inputted in the X-ray tube 107. The gantry controller 111 is a device which controls circumferential rotating operations of the X-ray tube 107 and the X-ray detector 108, with a Z-axis direction as a circumferential rotation axis. The bed controller 112 is a device which controls up-and-down, back-and-forth and left-and-right movements of the bed 102. The detector controller 113 is a device which controls the X-ray detector 108. In the X-ray CT apparatus, generally, image sensing is performed about 1,000 times per cycle in a circumferential direction. The image sensing at once is referred to as a unit "1 view". An image sensing aspect that during X-ray generation, the bed 102 is fixed, and the X-ray tube 107 and the X-ray detector 108 perform image sensing while circulating around the subject 106 in a circular orbital shape is referred to as axial scanning, normal scanning, conventional scanning, or the like. On the other hand, an image sensing aspect that during X-ray generation, the bed 102 is continuously moved in a circumferential rotation axis (Z-axis) direction, and the X-ray tube 107 and the X-ray detector 108 perform image sensing while circulating around the subject 106 in a helical orbital shape is referred to as helix scanning, helical scanning, spiral scanning, or the like (hereinafter, presented as "helix scanning"). Further, when a tomographic image of a heart of the subject 106 is generated with the X-ray CT apparatus, an electrocardiographic-waveform acquisition device 109 is provided, to obtain an electrocardiographic waveform as a biological signal of the subject 106 and transmit the electrocardiographic waveform to an image creation unit 115 to be described later.

The console 103 is provided with a system controller 114, the image creation unit 115, an image display unit 116, and an operation unit 117. The system controller 114 receives an input from the operation unit 117, and controls the entire X-ray CT apparatus. Specifically, the system controller 114 controls the X-ray controller 110, the gantry controller 111, the bed controller 112, and the detector controller 113 in accordance with image sensing conditions set with the operation unit 117, and controls the image creation unit 115 in accordance with image reconstruction conditions set with the operation unit 117. The image creation unit 115 performs image reconstruction processing using projection data sent with the detector controller 113 from the X-ray detector 108, and generates an image.

The image display unit 116 is provided with a display 104 to display a reconstruction condition setting screen or an image. Further, the operation unit 117 is provided with a keyboard 105A to input the subject's name, inspection date and time, and the like, a mouse 105B to indicate a mouse pointer position projected on the display 104, and the like.

Since a heart repeats contraction/expansion motion at a constant period, it is necessary to suppress occurrence of motion artifact by the contraction/expansion motions. As an image sensing method for generating a tomographic image of a heart, with this purpose, two types of methods, i.e., retrospective scanning and prospective scanning are given. In the prospective scanning, axial scanning is performed in synchronization with an electrocardiographic waveform from the electrocardiographic-waveform acquisition device 109. The electrocardiographic waveform is monitored, and when a specific time phase (e.g., an R-wave) is detected, then after a designated delay time, an X-ray is irradiated to perform axial scanning. Since the X-ray is irradiated only in the time phase where the heart movement is small, invalid exposure is small. However, it is difficult to perform image sensing with respect to heart rate variability and high heart rate. On the other hand, in the retrospective scanning, the electrocardiographic waveform of the subject 106 is obtained while helix scanning is performed. After acquisition of projection data and the electrocardiographic waveform, projection data in the time phase where the heart movement is small (systole/diastole) is extracted with electrocardiographic waveform information, and image reconstruction is performed with only the extracted projection data. In reconstruction, it is possible to generate a tomographic image where motion artifacts due to heart movement is suppressed by using only the projection data in the cardiac phase where the heart movement is small.

For reconstruction of the heart image by retrospective scanning, segment reconstruction is used. In the segment reconstruction, reconstruction is performed with projection data in the same time phase from plural heart rates. When the heart rate is low (the heart movement is slow), it is possible to perform reconstruction only with projection data within 1 heartbeat. When the heart rate is high (the heart movement is fast), motion artifacts appear only with the projection data within 1 heartbeat, accordingly, projection data only in the same time phase are collected from plural heart rate projection data, and reconstruction is performed. The segment reconstruction will be described by using FIG. 18. Image positions 701 and 702 are respectively an image position where a tomographic image of the heart of the subject 106 is generated from the projection data. The tomographic image is reconstructed with the projection data obtained from a segment range defined as a vicinity around the image positions 701 and 702. FIG. 18(a) shows an example where helices 703 and 704 are included in the segment range to form a tomographic image in the image position 702. Figure (b) shows an example where the helices 703, 704, and 705 are included in the segment range to form a tomographic image in the image position 701. For this purpose, in the image position 702, a tomographic image is generated from projection data of segments 711 and 712 for two heartbeats (the number of segments is 2). In the image position 701, a tomographic image is generated from projection data of segments 713, 714, and 715 for three heartbeats (the number of segments is 3). Note that to form a tomographic image, the total number of views of projection data of plural segments must be equal to or more than half cycle. Accordingly, the segment size in formation of a tomographic image when the number of segments is 2 and the segment size in formation of a tomographic image when the number of segments is 3 (for example, the size of the segment 711 and the size of the segment 713) are different. Further, in the image reconstruction, reverse projection is performed with weighting by view, accordingly, the shape of weighting of the segment with respect to each view is referred to as a "view weight".

Figure 3:
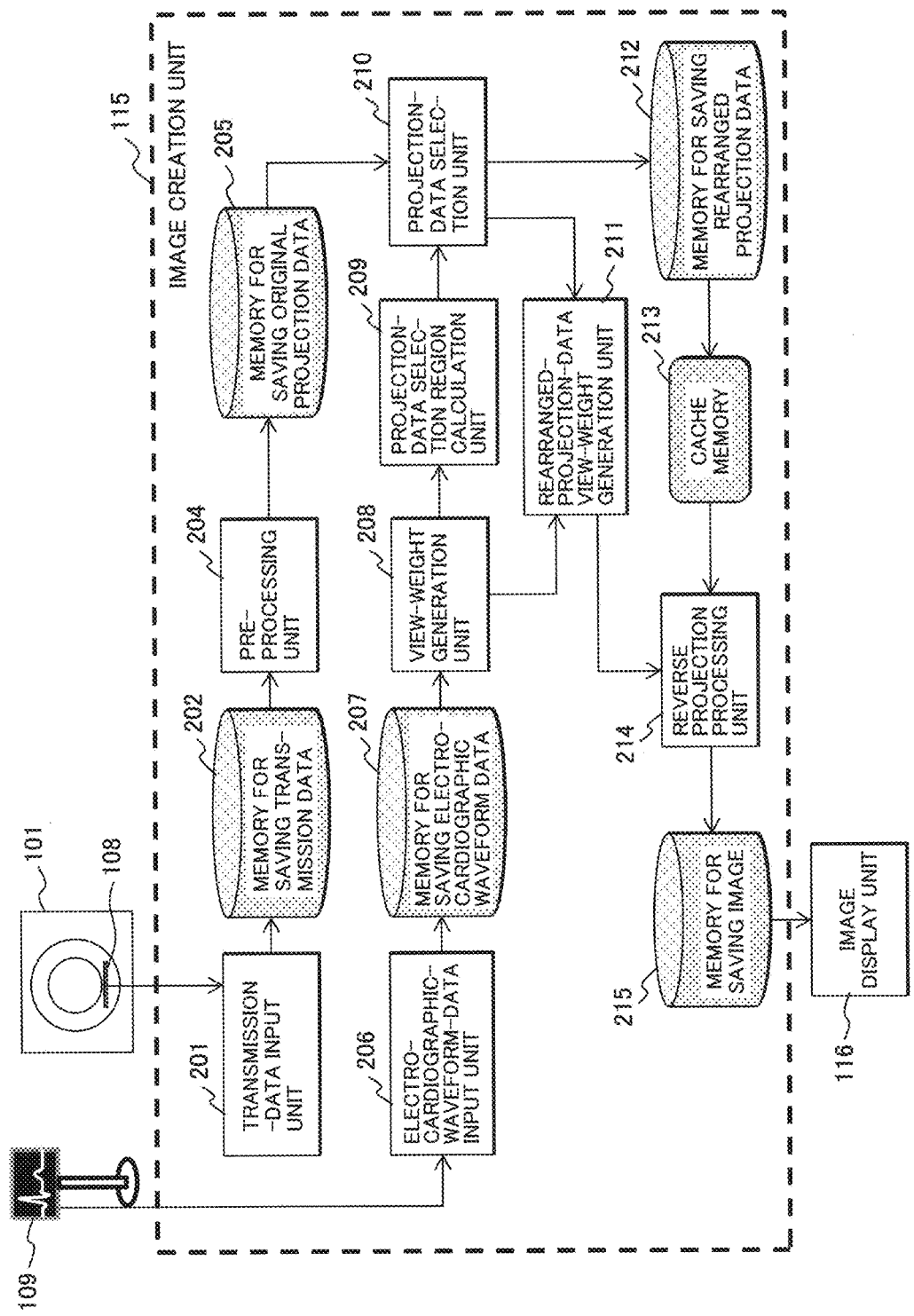
FIG. 3 is a diagram explaining the details of processing in an image creation unit.

FIG. 3 shows the details of processing in the image creation unit 115. The X-ray is irradiated from the X-ray tube 107 of the scanner 101 toward the subject 106, then the X-ray detector 108 detects X-ray transmitted through the subject 106, and sends the detected X-ray as transmission data to a transmission-data input unit 201. The transmission-data input unit 201 writes the obtained transmission data into a memory 202 for saving transmission data. On the other hand, the electrocardiographic-waveform acquisition device 109 sends the electrocardiographic waveform of the subject 106 to an electrocardiographic-waveform-data input unit 206. The electrocardiographic-waveform-data input unit 206 writes the received electrocardiographic waveform data into a memory 207 for saving electrocardiographic waveform data.

A pre-processing unit 204 reads the transmission data from the memory 202 for saving transmission data, performs pre-processing to generate projection data (original projection data), and writes the projection data into a memory 205 for saving original projection data. Note that the pre-processing is to perform various processing such as correction with respect to transmission data as raw data for improvement of CT value accuracy and image quality.

The view-weight generation unit 208 reads the electrocardiographic waveform from the memory 207 for saving electrocardiographic waveform data, and with reference to the electrocardiographic waveform, generates view weights for reverse projection for the entire image, with the projection data in a specific cardiac phase.

A projection-data selection region calculation unit 209 calculates a projection data selection region necessary for reverse projection of the entire image, with reference to the view weights for the entire image generated with the view-weight generation unit 208. A projection-data selection unit 210 reads only projection data necessary for the reverse projection from the memory 205 for saving original projection data with the projection data selection region calculated with the projection-data selection region calculation unit 209, then performs rearrangement, and writes the rearranged data into a memory for saving rearranged projection data 212. A rearranged-projection-data view-weight generation unit 211 regenerates view weights for the entire image in correspondence with the projection data rearranged with the projection-data selection unit 210 (rearranged projection data).

A reverse projection processing unit 214 generates a tomographic image with the projection data rearranged with the projection-data selection unit 210 and written into the memory for saving rearranged projection data 212 (rearranged projection data) and the view weights generated with the rearranged-projection-data view-weight generation unit 211, and writes the tomographic image into the memory for saving image 215. In this tomographic image generation work, the number of times of access to the memory 212 is reduced by temporarily storing the projection data read from the memory for saving rearranged projection data 212 (main memory) into a cache memory 213.

The image display unit 116 reads the tomographic image from the memory for saving image 215, and displays the tomographic image on the display 104. Further, parameters regarding image reconstruction are displayed on the display 104. It is possible to change the parameters via the operation unit 117.

EXAMPLE 1

Hereinbelow, Example 1 will be described. The respective functional blocks described in FIG. 3, such as the pre-processing unit 204, the view-weight generation unit 208, the projection-data selection region calculation unit 209, the projection-data selection unit 210, the rearranged-projection-data view-weight generation unit 211, and the reverse projection processing unit 214, are realized with general computer hardware, and realized by executing a program corresponding to the respective functional blocks with a processor of the computer. Generally, when the processor executes calculation, the processor reads necessary data from a main memory, performs the calculation, and writes the calculation result into the main memory again. With advance of speed in processors in recent years, when the transfer speed between the processor and the main memory cannot catch up with the processing speed of the processor, the processor becomes in a data waiting state from the main memory. To prevent occurrence of this waiting state, a cache memory is provided between the processor and the main memory. That is, by previously transferring data required by the processor from the main memory to the cache memory, it is possible to prevent processing delay in the processor which may be caused by access to the main memory. Although the cache memory has a small capacity, it is accessible at a high speed. Specifically, in parallel to the calculation execution cycle of the processor, continuous data in a size integer multiple of a cache line size is transferred from the main memory to the cache memory. When the data used in the next calculation execution cycle is transferred to the cache memory, the processor reads the data from the high-speed cache memory, thus data waiting does not occur.

Figure 4:
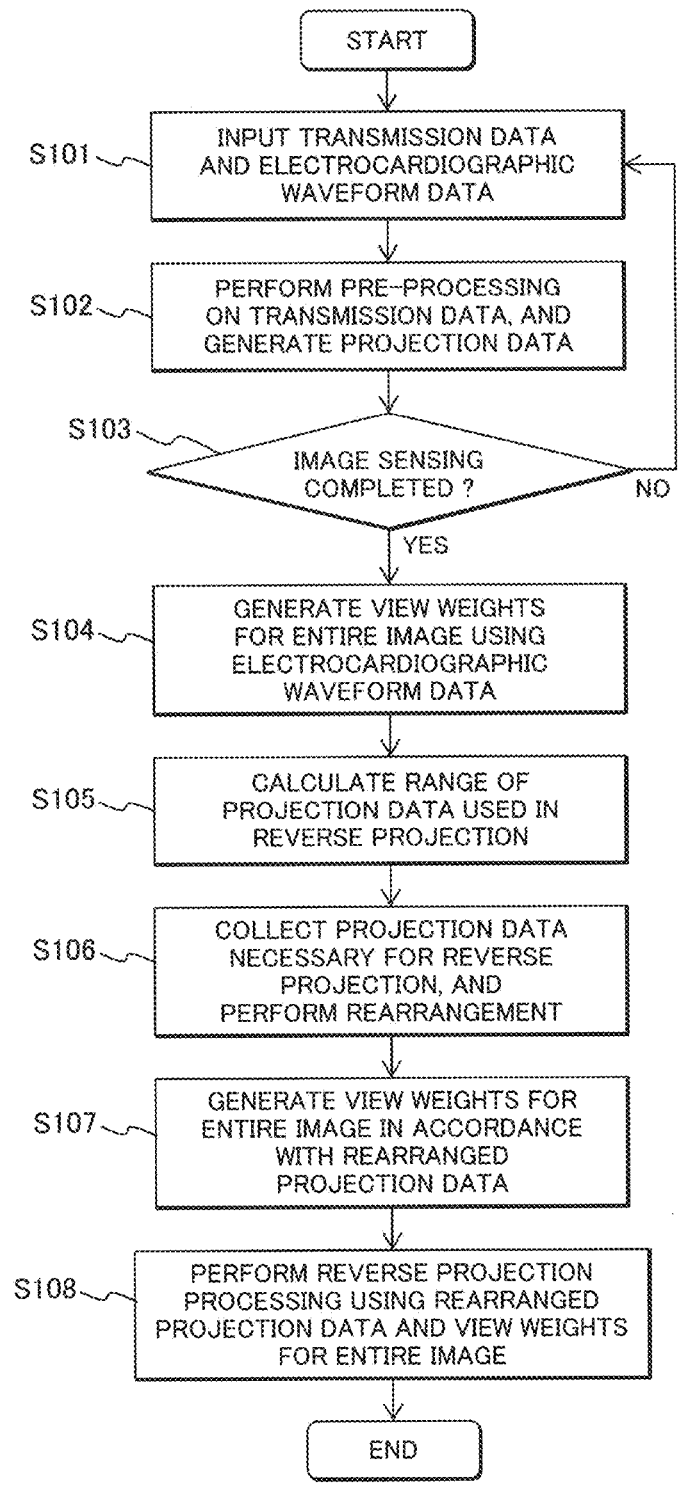
FIG. 4 is a flowchart of Example 1.

However, when data necessary for calculation does not exist on the cache memory, the processor reads the necessary data from the main memory (this is referred to as "cache miss"), which causes data waiting. Accordingly, it is important to increase the probability that necessary data exists on the cache memory (referred to as a "cache hit ratio") from the point of view of increasing of processing speed. To increase the cache hit ratio, processing in the respective blocks in Example 1 will be described by using the flowchart of FIG. 4.

(Step S101)

The transmission-data input unit 201 writes the transmission data sent from the X-ray detector 108 into the memory 202 for saving transmission data. The electrocardiographic-waveform-data input unit 206 writes the electrocardiographic waveform data sent from the electrocardiographic-waveform acquisition device 109 into the memory 207 for saving electrocardiographic waveform data.

(Step S102)

The pre-processing unit 204 reads the transmission data from the memory 202 for saving transmission data, performs pre-processing on the read data to generate projection data (original projection data), and writes the projection data into the memory 205 for saving original projection data.

(Step S103)

It is determined whether or not the image sensing has been completed. When it is determined that the image sensing has not been completed, the processing returns to step S101. When it is determined that the image sensing has been completed, the processing proceeds to step S104.

(Step S104)

The view-weight generation unit 208 generates view weights for the entire image with the electrocardiographic waveform data. The details of the processing in the view-weight generation unit 208 will be described by using FIG. 5.

Figure 5:
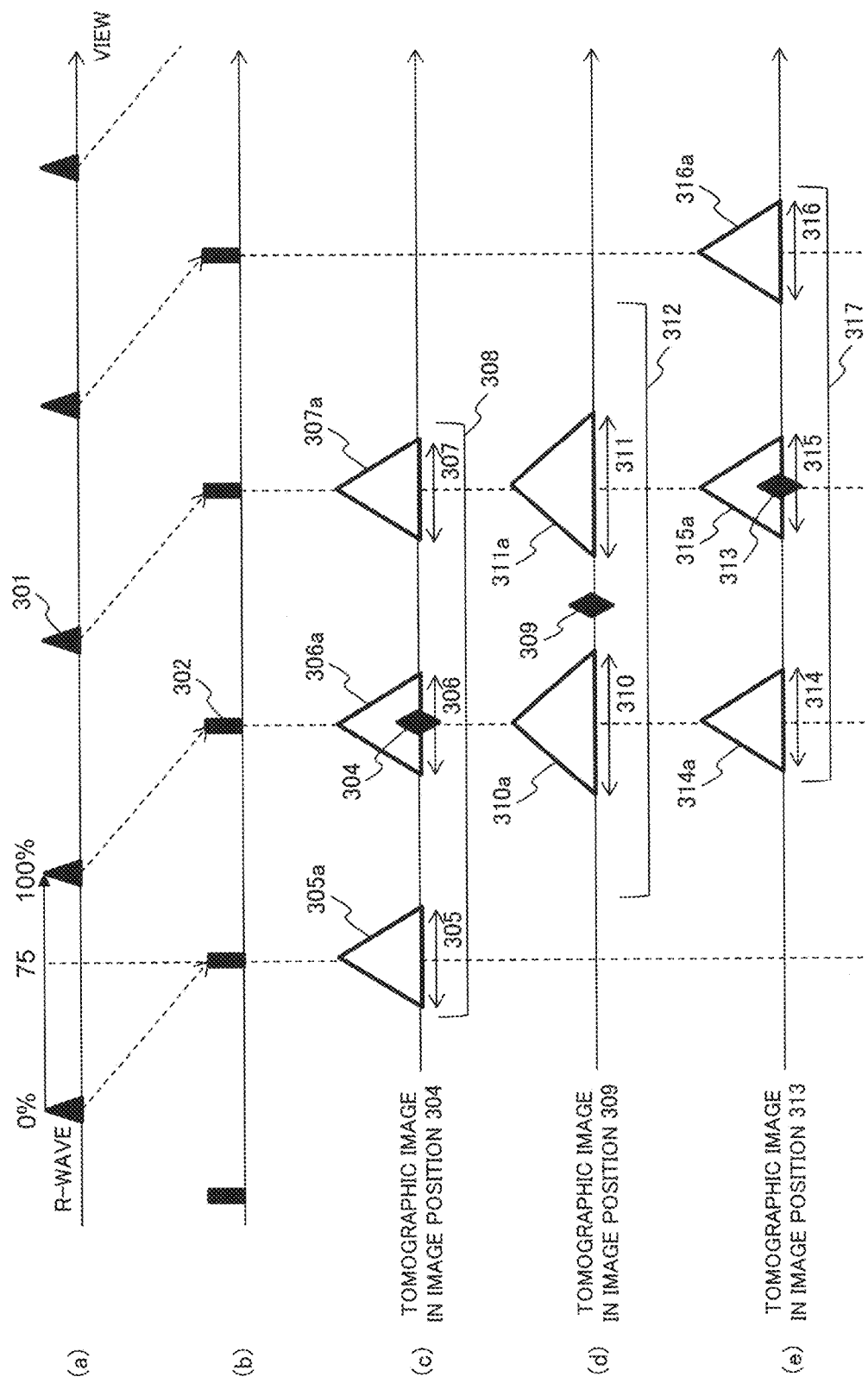
FIG. 5 is a diagram explaining the details of processing in a view-weight generation unit.

In FIG. 5, the respective horizontal axes indicate views. The electrocardiographic waveform is read from the memory 207 for saving electrocardiographic waveform data, and the position of an R-wave 301 is examined in the electrocardiographic waveform (a). Then, by shifting from the position of the R-wave by specific time phase, a segment position 302 is determined (b). For example, when the specific time phase is shifted relatively, with adjacent R-wave-R-wave interval as 0-100%, the specific time phase is set from 0 to 100%. Since the contraction/expansion state in the heart appears in the electrocardiographic waveform, a time phase where the heart movement is small is set based on the electrocardiographic waveform. In the example of FIG. 5, it is determined that the time phase where the heart movement is small corresponds to the position of 75% in the R-wave-R-wave interval, and the position of 75% is set as the segment position.

FIG. 5 shows an example where tomographic images are generated with regard to image positions 304, 309, and 313, mutually shifted in a Z-direction. The segment is set in correspondence with a segment position existing within a segment range, defined around an image position to generate a tomographic image, and a view weight is set with respect to each of projection data included in each segment. In the case of a tomographic image in the image position 304 (c), three segments 305, 306, and 307 exist in a segment range 308 around the image position 304. View weights 305a, 306a, and 307a are set in the respective segments. Note that in this example, the view weight is increased and decreased in front and behind the view weight of the projection data in the segment position 302 as a maximum view weight. However, it is not limited to this pattern, and it can be arbitrarily determined in accordance with image sensing conditions. In the case of a tomographic image in the image position 309 (d), two segments 310 and 311 exist in a segment range 312 around the image position 309. View weights 310a and 311a are set in the respective segments. In the case of a tomographic image in the image position 313 (e), three segments 314, 315, and 316 exist in a segment range 317 around the image position 313. View weights 314a, 315a, and 316a are set in the respective segments. As described above, to generate a tomographic image by reverse projection, projection data, the number of views of which s equal to or more than at least the half cycle are required. Accordingly, when the number of segments is large (c, e), the width of 1 segment is small. When the number of segments is small (d), the width per segment is large.
(Step S105)

Figure 6:
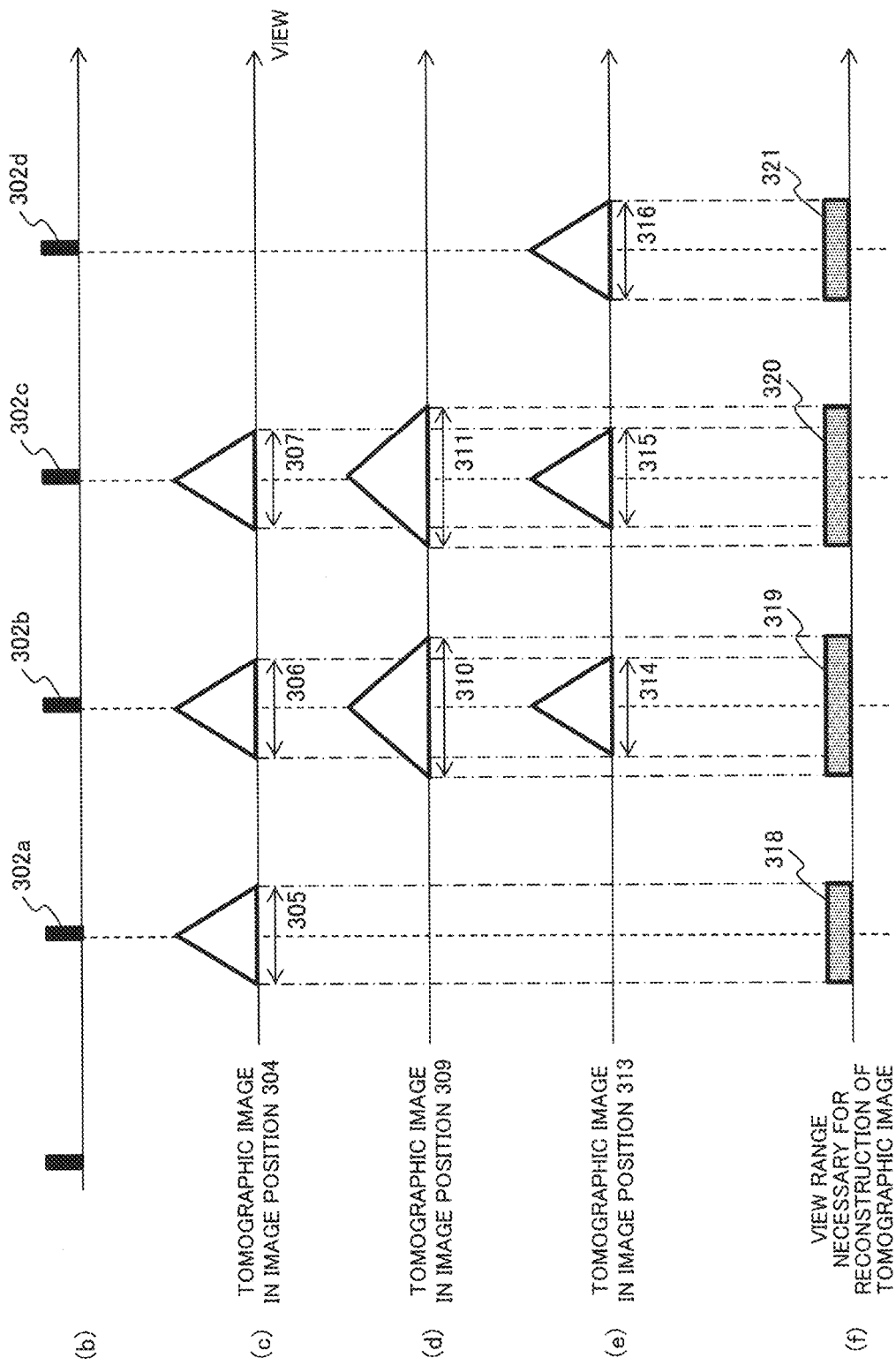
FIG. 6 is a diagram explaining the details of processing in a projection-data selection region calculation unit.

The projection-data selection region calculation unit 209 calculates the range of projection data used in the reverse projection. The details of the processing in the projection-data selection region calculation unit 209 will be described by using FIG. 6. In FIG. 6, the respective horizontal axes also indicate views.

The projection-data selection region calculation unit 209 overlays the segments with respect to the respective tomographic images generated with the view-weight generation unit 208, and calculates a view range necessary for the reverse projection. Since there is no other segment to be overlaid on the segment 305 in the image position 304 in a segment position 302a, as a result, a view range 318 is the same as that of the segment 305. On the other hand, in a segment position 302b, the segment 306 in the image position 304, the segment 310 in the image position 309, and the segment 314 in the image position 313 are overlaid. Among them, as the segment with a maximum width is the segment 310 where the number of segments is 2, the width of a view range 319 after the overlay is the same as that of the segment 310. Similarly, in a segment position 302c, the segment 307 in the image position 304, the segment 311 in the image position 309, and the segment 315 in the image position 313 are overlaid. Among them, since the segment with a maximum width is the segment 311 where the number of segments is 2, the width of a view range 320 after the overlay is the same as that of the segment 311. Further, in a segment position 302d, since there is no other segment to be overlaid on the segment 316 in the image position 313, as a result, a view range 321 is the same as that of the segment 316. The view ranges 318, 319, 320, and 321 thus calculated indicate regions necessary for generation of tomographic images in the image positions 304, 309, and 313 (f). Note that in the description of the example in FIG. 6, the number of tomographic images is 3, however, the number of tomographic images is not particularly limited, but it is determined in accordance with image sensing conditions. The number of tomographic images may be 1. Further, a necessary region is calculated with a segment width, and the shape of view weight in the segment is not particularly limited.
(Step S106)

Figure 7:
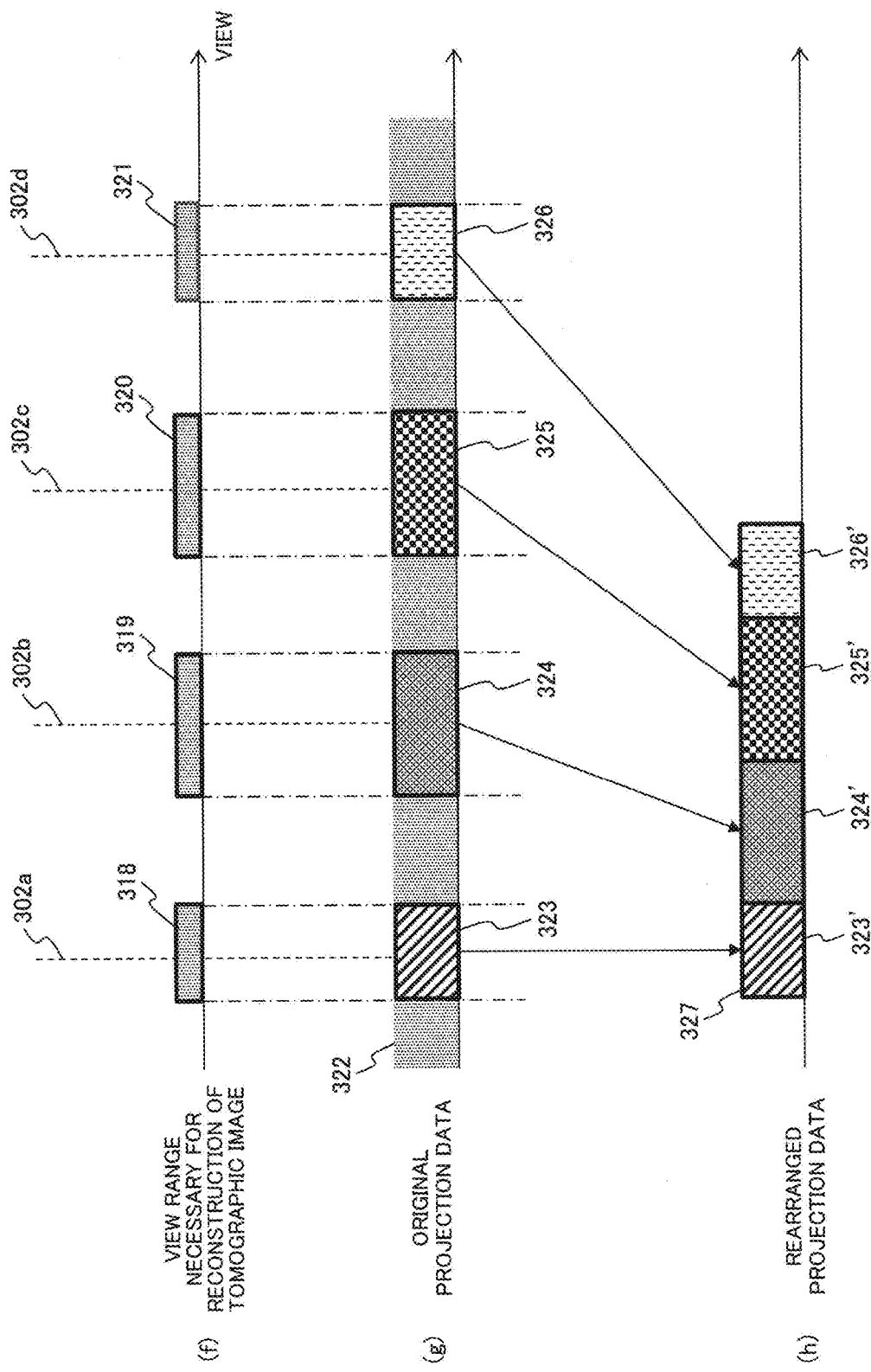
FIG. 7 is a diagram explaining the details of processing in a projection-data selection unit.

The projection-data selection unit 210 rearranges the projection data such that it is only projection data necessary for reverse projection. The details of the processing in the projection-data selection unit 210 will be described by using FIG. 7. In FIG. 7, the respective horizontal axes also indicate views.

The projection-data selection unit 210 reads projection data necessary for the reverse projection with the view ranges 318, 319, 320, and 321 calculated with the projection-data selection region calculation unit 209, i.e., the projection data 323, 324, 325, and 326 corresponding to the view ranges 318, 319, 320, and 321, from projection data (original projection data) 322 stored in the memory for saving original projection data 205 (g). Then the projection-data selection unit 210 writes projection data (rearranged projection data) 327, rearranged by connecting the read projection data, into the memory for saving rearranged projection data 212 (h).
(Step S107)

Figure 8:
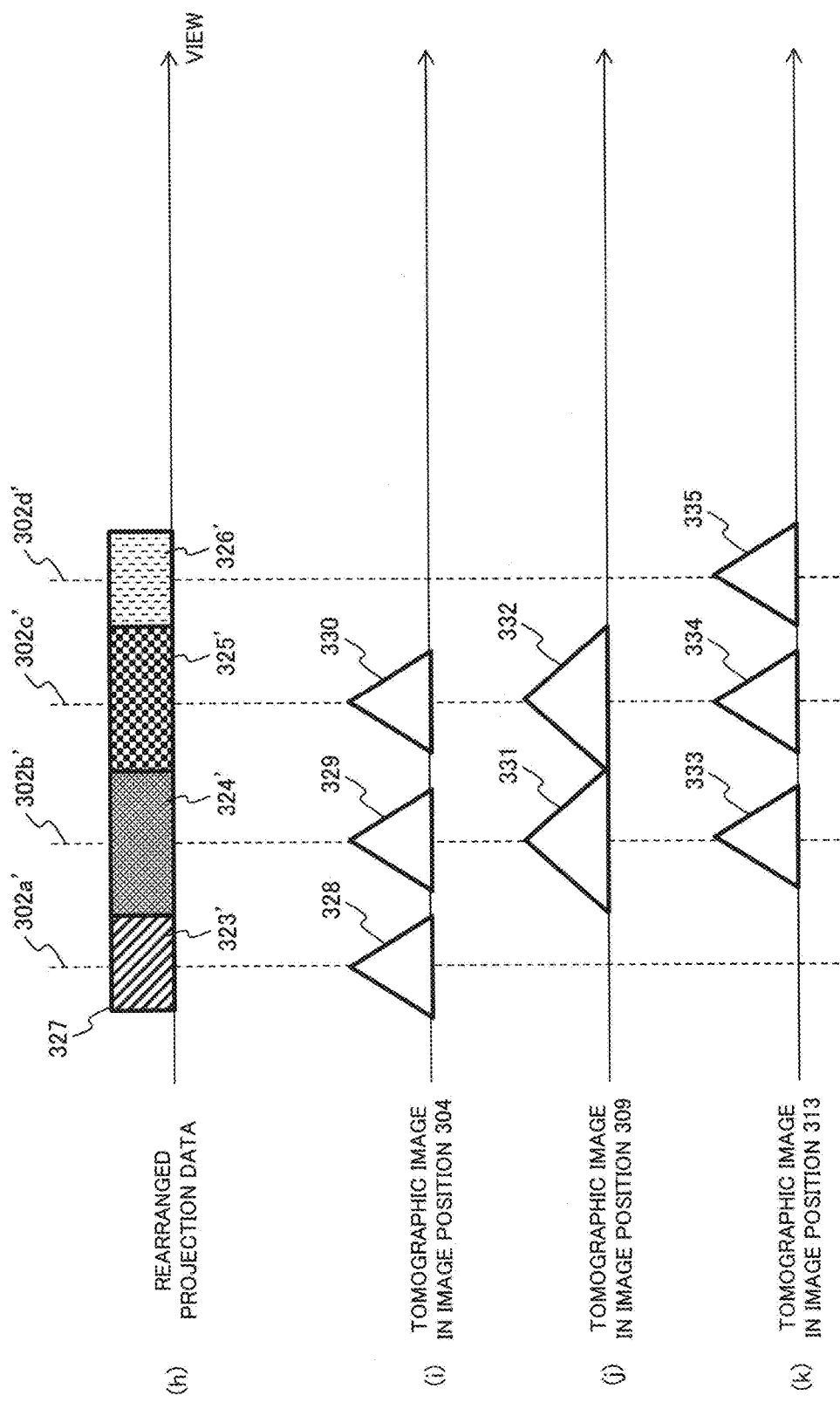
FIG. 8 is a diagram explaining the details of processing in a rearranged-projection-data view-weight generation unit.

The rearranged-projection-data view-weight generation unit 211 generates view weights for the entire image in correspondence with the projection data rearranged with the projection-data selection unit 210. The details of the processing in the rearranged-projection-data view-weight generation unit 211 will be described by using FIG. 8. In FIG. 8, the respective horizontal axes also indicate views.

The rearranged-projection-data view-weight generation unit 211 generates the view weights of respective segments to generate a tomographic image in respective image positions with respect to the projection data (rearranged projection data) 327 rearranged with the projection-data selection unit 210. The number of segments and the shape of the view weight are the same as those generated with the view-weight generation unit 208 with respect to the initial projection data (original projection data) 322. However, as the projection data is rearranged, the positions of the view weights are changed. Specifically, the view weights are provided such that centers 302a', 302b', 302c', and 302d' of respective segments 323', 324', 325' and 326' of the projection data 327 correspond with the centers of the view weights.

In the case of the tomographic image in the image position 304 (i), three segments 323', 324', and 325' of the rearranged projection data 327 are used. Since all the projection data of the segments 324' and 325' is not used, view weights 328, 329, and 330 are not adjacent to each other. However, the interval between these view weights is narrow in comparison with the view weights 305a, 306a and 307a generated with the view-weight generation unit 208 (see FIG. 5). In the case of the tomographic image in the image position 309 (j), since all the projection data of the two segments 324' and 325' of the rearranged projection data 327 is used, the view weights 331 and 332 are adjacent to each other. In the case of the tomographic image in the image position 313 (k), three segments 324', 325', and 326' of the rearranged projection data 327 are used. Since all the projection data of the segments 324' and 325' is not used, the view weights 333, 334, and 335 are not adjacent to each other. However, the interval between these view weights is narrow in comparison with the view weights 314a, 315a, and 316a generated with the view-weight generation unit 208 (see FIG. 5).

(Step S108)

The reverse projection processing unit 214 generates a tomographic image by performing reverse projection processing with the projection data (rearranged projection data) 327 rearranged with the projection-data selection unit 210 and the view weights 328 to 335 generated with the rearranged-projection-data view-weight generation unit 211. At this time, the projection data moved from the main memory (memory for saving rearranged projection data 212) to the cache 213 is always used in the reverse projection processing, thus the cache hit ratio is improved.

As described above, in Example 1, since the size of projection data moved from the main memory to the cache small in comparison with the conventional art, and the projection data moved to the cache is always used in the reverse projection, it is possible to improve the cache hit ratio.

Further, since it is assumed that the projection data is accessed sequentially from the top view, hardware prefetch effectively works by the sequential access from the top on the memory, and it is possible to improve the cache hit ratio. This leads to reduction of processing time of the reverse projection, and the work flow of CT inspection is improved.

Note that the description has been made in the example of heart image sensing, although the present invention is not limited to the heart image sensing. For example, in the case of CT image sensing by using respiration synchronization, it is possible to apply the technique of Example 1 by utilizing inhalation-exhalation as a biological signal and handling it as in the case of the electrocardiographic waveform information.

EXAMPLE 2

Figure 9:
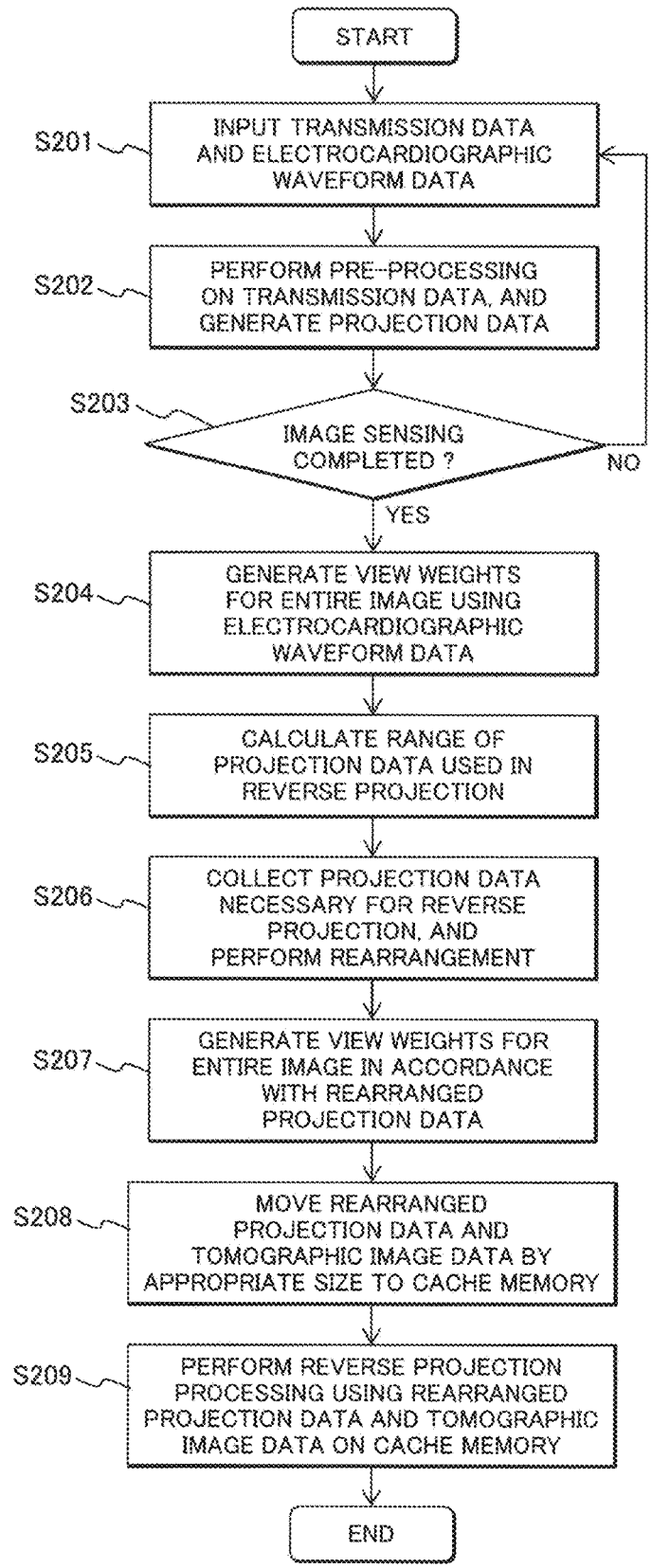
FIG. 9 is a flowchart of Example 2.

In Example 2, the improvement of efficiency of utilization of the cache memory will be described by using FIG. 9.

(Step S201 to Step S207)

Since step S201 to step S207 are the same as step S101 to step S107 respectively described in Example 1, explanations of these steps will be omitted.

(Step S208)

Figure 10:
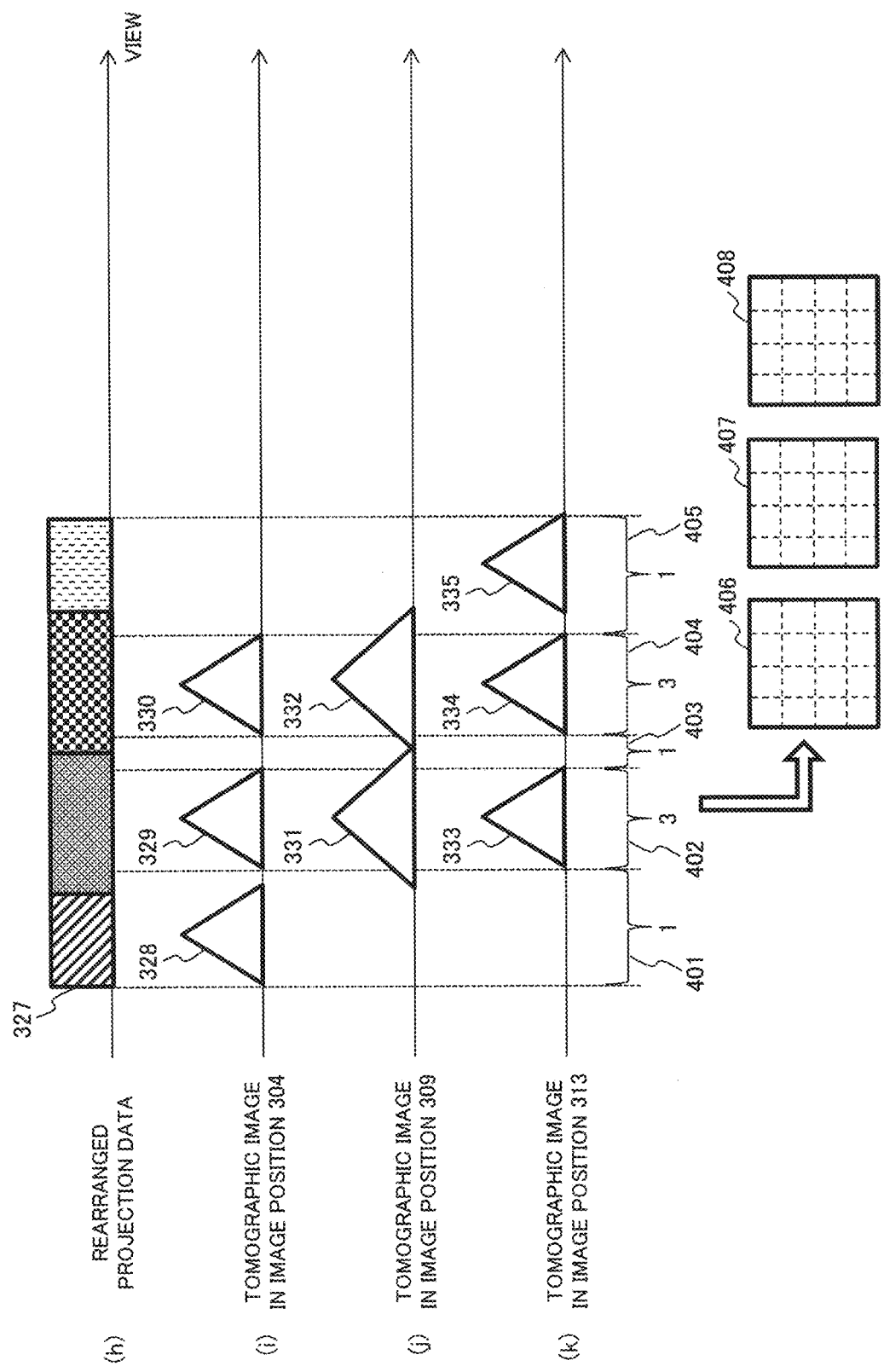
FIG. 10 is a diagram explaining the way of obtaining the number of views placed in a cache memory.

The number of tomographic images for simultaneous reverse projection in the respective views of the projection data is examined with the view weights 328 to 335 generated with the rearranged-projection-data view-weight generation unit 211. FIG. 10 shows the result. (h) to (k) are the same as those in FIG. 8. In a view range 401 on the projection data 327, the number of tomographic images for which the respective views subjected to reverse projection is "1", and the images subjected to reverse projection are "the tomographic image in the image position 304" and "the tomographic image in the image position 309". In a view range 402 on the protection data 327, the number of tomographic images for which the respective views are subjected to reverse projection is "3", and the images subjected to reverse projection are "the tomographic image in the image position 304", "the tomographic image in the image position 309", and "the tomographic image in the image position 313". In a view range 403 on the projection data 327, the number of tomographic images for which the respective views are subjected to reverse projection is "1", and the image subjected to reverse projection is "the tomographic image in the image position 309". In a view range 404 on the projection data 327, the number of tomographic images for which the respective views are subjected to reverse projection is "3", and the images subjected to reverse projection are "the tomographic image in the image position 304", "the tomographic image in the image position 309", and "the tomographic image in the image position 313". In a view range 405 on the projection data 327, the number of tomographic images for which the respective views subjected to reverse projection is "1", and the images subjected to reverse projection are "the tomographic image in the image position 309" and "the tomographic image in the image position 313".

For example, in the case of the view range 402 on the projection data 327, the images subjected to reverse projection are a tomographic image 406 in the image position 304, a tomographic image 407 in the image position 309, and a tomographic image 408 in the image position 313. Assuming that the size per image is 1 MB (512 pixels×512 pixels×4 bytes), the size of three images is 3 MB. On the other hand, regarding the size of projection data per view, it is assumed that the size is 0.25 MB (1024 ch×64 slices×4 bytes). When the size of the cache memory 213 is 20 MB, assuming that about the half is saved in consideration of use of the cache memory 213 in other processing, the cache size available in reverse projection is 10 MB. When 3 MB is used for tomographic images and the remaining 7 MB is used for projection data, it is possible to place projection data for 28 views (=7 MB÷0.25 MB) on the cache memory 213.

(Step S209)

Figure 11:
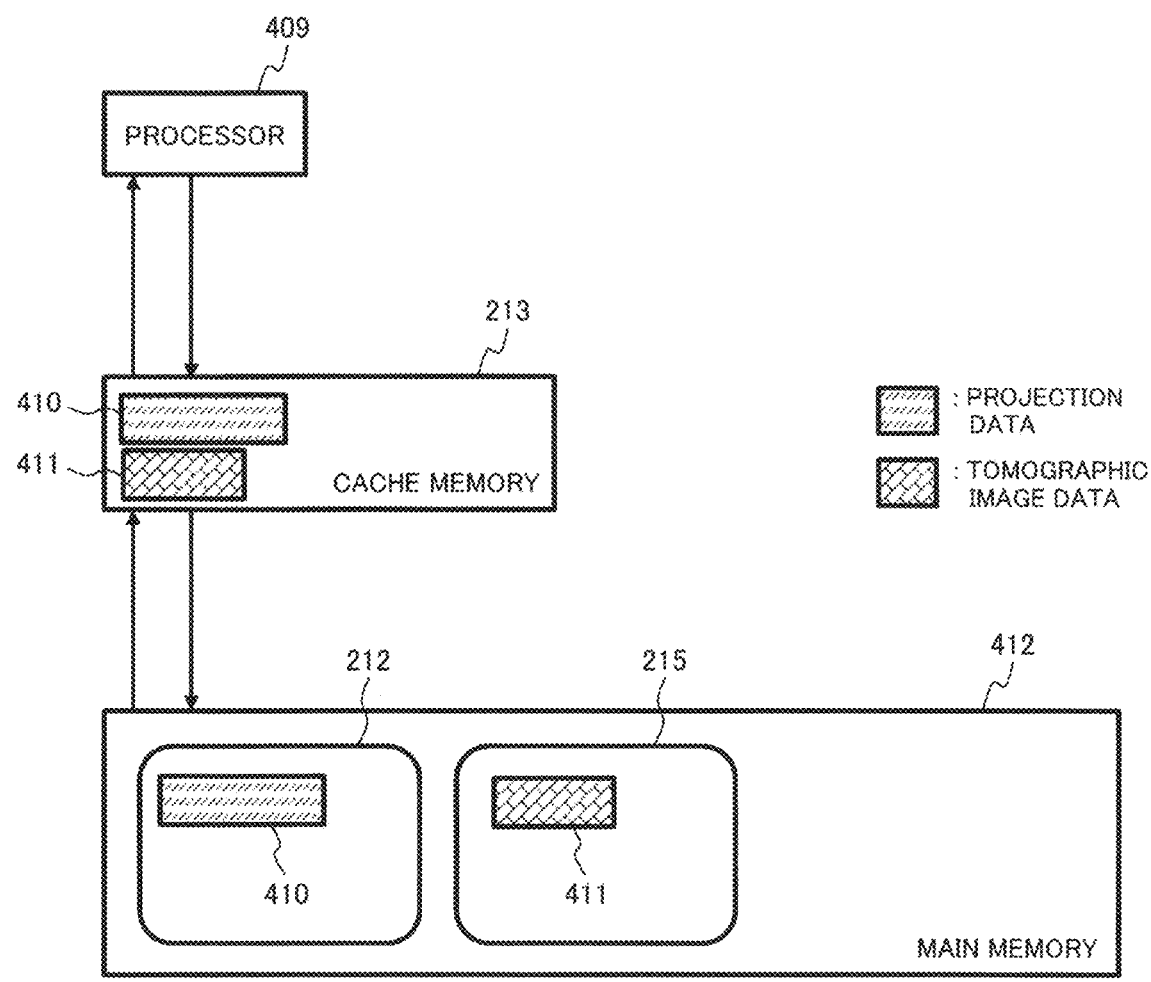
FIG. 11 is a diagram showing the relationship among a processor, the cache memory, and a main memory.

The relationship among a processor 409, a main memory 412, and the cache memory 213 for reverse projection processing with the cache memory 213 will be described by using FIG. 11. When the processor 409 reads data from the main memory 412 for the reverse projection processing, the data is temporarily moved to the cache memory 213, then the processor 409 reads the data from the cache memory 213. The result of calculation with the read data is written into the cache memory 213, then is written from the cache memory 213 into the main memory 412. When the processor 409 next uses the same data, the processor 409 accesses the data which exists on the cache memory 213. The speed of data transfer is higher between the processor 409 and the cache memory 213 than between the cache memory 213 and the main memory 412. Accordingly, it is desirable to reutilize the data on the cache memory 213 as much as possible.

Accordingly, when the view range 402 on the projection data 327 is reverse-projected (see FIG. 10), by moving tomographic image data 411 for three images and projection data 410 for 28 views from the main memory 412 to the cache memory 213, it is possible to improve the cache hit ratio since the data necessary for the reverse projection exist on the cache memory 213. When all the protection data 410 for 28 views have been used in the reverse projection processing, the next projection data for 28 views is moved from the main memory 412. As the old projection data is not accessed, the old projection data disappears from the cache memory 213. Regarding the tomographic image data for three images, it is not changed as long as the reverse projection is performed with the projection data in the view range 402 of the projection data 327, it remains on the cache memory 213.

In the next view range 403 of the projection data 327, the number of images subjected to reverse projection is 1, i.e., only the tomographic image 407 in the image position 309. Accordingly, only tomographic image data for one image (1 MB) is placed on the cache memory 213. The remaining 9 MB for reverse projection can be allocated to projection data. In this case, it is possible to move protection data for 36 views (9 MB÷0.25 MB) to the cache memory 213. In this manner, by dividing a view range in correspondence with the number of tomographic images for simultaneous reverse projection in the respective views of the projection data 327, first ensuring tomographic image data for simultaneous reverse projection from the cache memory capacity allocated to the reverse projection, and using the remaining cache memory capacity for storage of projection data, it is possible to reduce cache miss as much as possible and to efficiently use the cache memory 213.

When a multi-core processor is used as the processor 409, in order to avoid conflict among the multiple cores regarding a writing destination of the calculation result of reverse projection (tomographic image), the tomographic image is divided into blocks and allocated to the multiple cores. In the example of FIG. 10, one tomographic image is divided into 16 blocks, although the number of blocks is not limited to this number. To increase the degree of parallelism of the multiple cores, it is desirable that the number of divided blocks is larger than the number of multiple cores. When the number of divided blocks is smaller than the number of multiple cores, some of cores are in a sleep state while other cores are performing calculation, thus all the multiple cores cannot be utilized.

As described above, by appropriately setting the number of views of projection data and the number of tomographic image data moved to the cache memory 213 within a predetermined view range of the projection data, it is possible to place all the data necessary for reverse projection on the cache memory 213. It is possible to improve the cache hit ratio, to enable reduction of processing time of the reverse projection, and to improve the workflow of CT inspection.

EXAMPLE 3

A heart constantly repeats pump motion to circulate blood in the body. In the pump motion, to search for a time phase where the heart movement is small (systole/diastole), tomographic images in plural time phases are generated at once, and a tomographic image in which the number of motion artifacts is the smallest (cardiac phase) may be found from the tomographic images. In Example 3, tomographic images in plural time phases are generated at once by applying Example 1.

Figure 12:
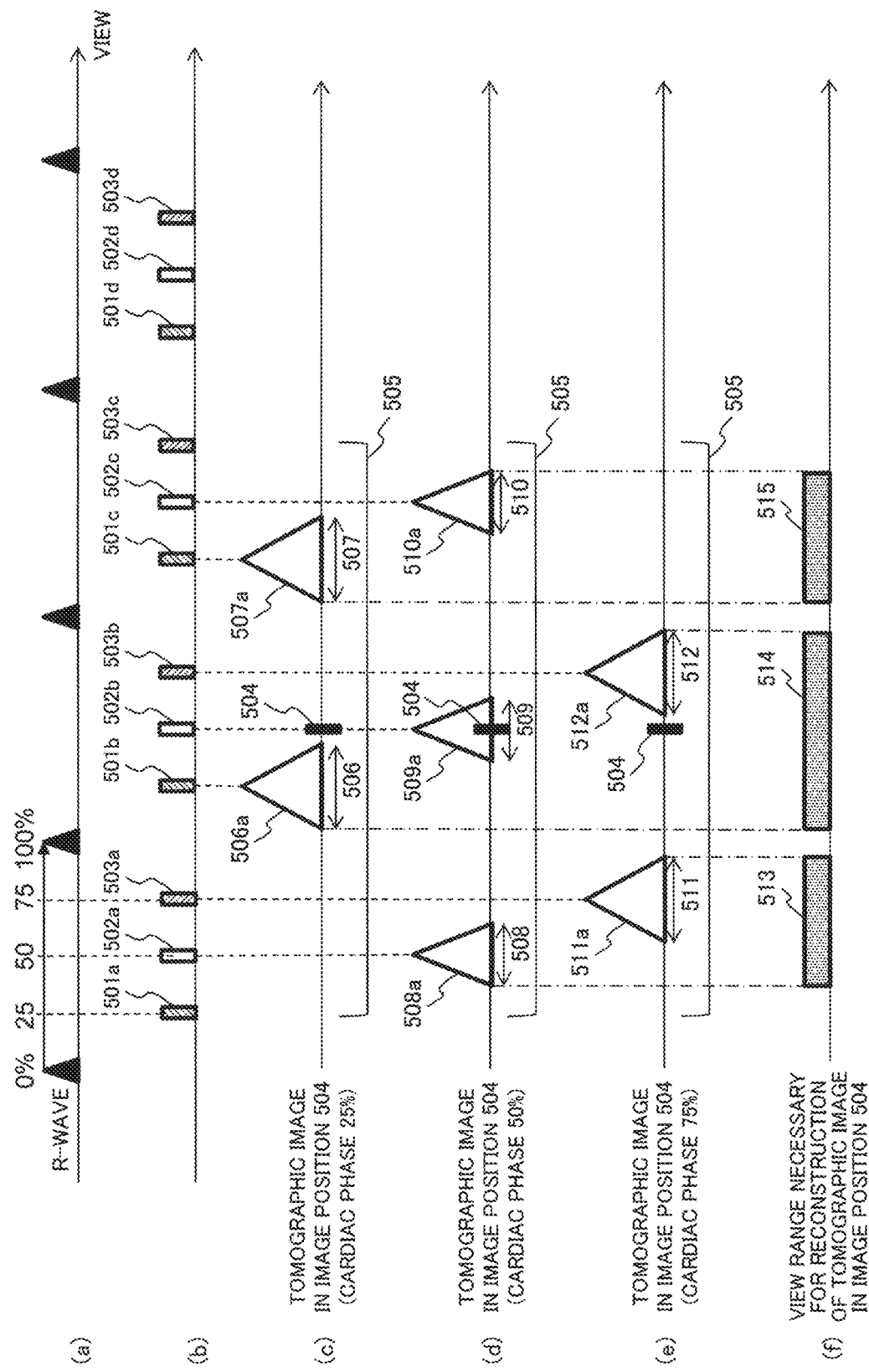
FIG. 12 is a diagram showing view weights for reverse-projecting a tomographic image in a first image position.

First, the view-weight generation unit 208 generates view weights in plural time phases in the respective images. FIG. 12 explains a method of calculating a view range necessary for tomographic image generation in a predetermined image position (image position 504), and shows an example where a view range is calculated, with the R-wave-R-wave interval as 0-100%, in correspondence with three cardiac phases (25%, 50%, and 75%). When the cardiac phase 25% is set as a segment position (c), two 25% cardiac phases 501b and 501c exist in a segment range 505 around the image position 504. Accordingly, segments 506 and 507 are set in correspondence with the cardiac phases 501b and 501c, and view weights 506a and 507a are set with respect to the respective segments. When the cardiac phase 50% is set as a segment position (d), three 50% cardiac phases 502a, 502b, and 502c exist in the segment range 505 around the image position 504. Accordingly, segments 508, 509, and 510 are set in correspondence with the cardiac phases 502a, 502b, and 502c, and view weights 508a, 509a, and 510a are set with respect to the respective segments. When the cardiac phase 75% is set as a segment position (e), two 75% cardiac phases 503a and 503b exist in the segment range 505 around the image position 504. Accordingly, segments 511 and 512 are set in correspondence with the cardiac phases 503a and 503b, and view weights 511a and 512a are set with respect to the respective segments.

The projection-data selection region calculation unit 209 generates view ranges 513, 514, and 515 necessary for tomographic image generation in the image position 504 by overlaying the segments set in correspondence with the three cardiac phases (25%, 50%, and 75%) (f). The view ranges 513 to 515 show view ranges necessary for tomographic image generation in all the cardiac phases in the image position 504.

Figure 13:
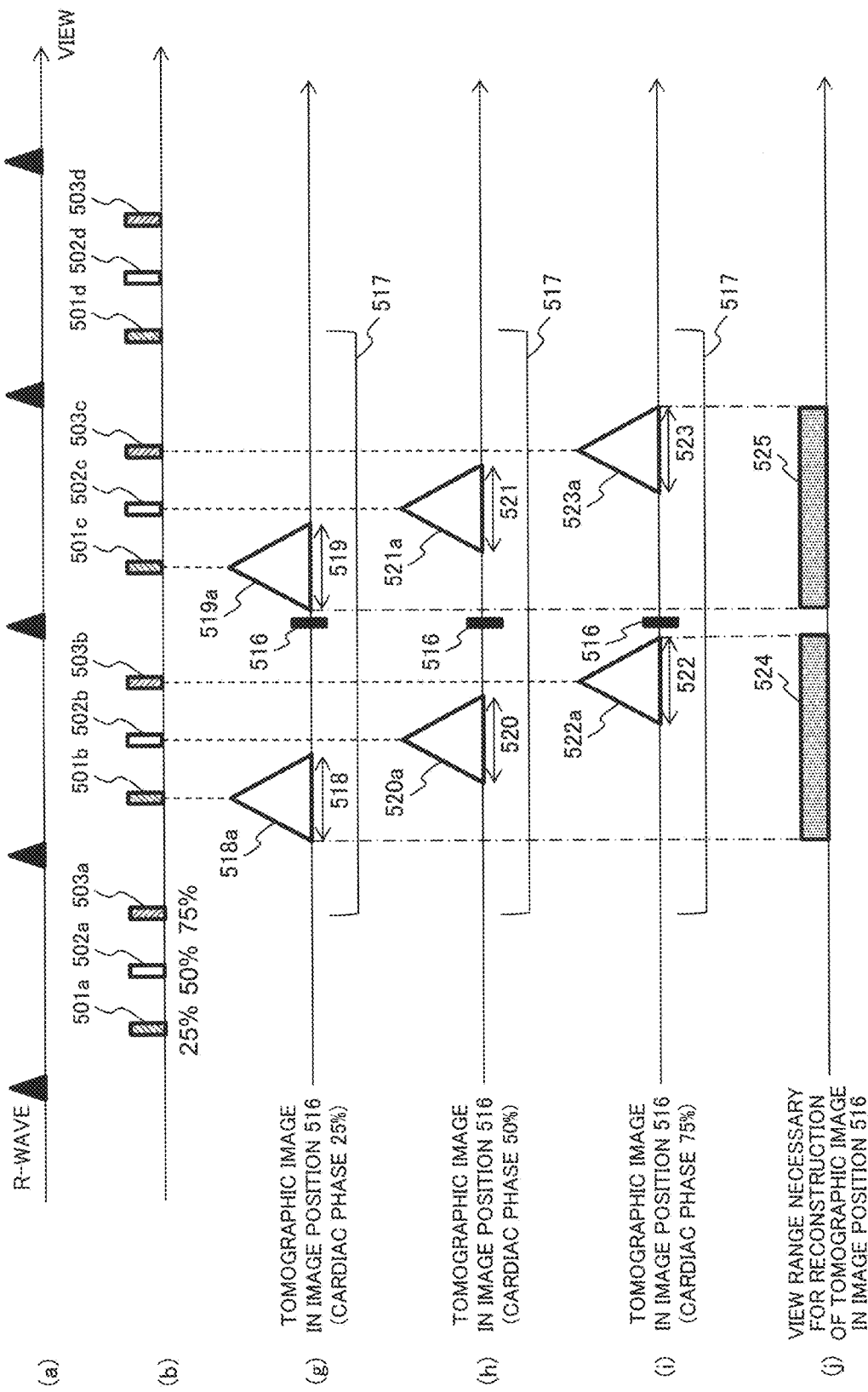
FIG. 13 is a diagram showing view weights for reverse-projecting a tomographic image in a second image position.

FIG. 13 explains a method of calculating a view range necessary for tomographic image generation in an image position 516 different from the image position 504. When the cardiac phase 25% is set as a segment position (g), two 25% cardiac phases 501b and 501c exist in a segment range 517 around the image position 516. Accordingly, segments 518 and 519 are set in correspondence with the cardiac phases 501b and 501c, and view weights 518a and 519a are set with respect to the respective segments. When the cardiac phase 50% is set as a segment position (h), two 50% cardiac phases 502b and 502c exist in the segment range 517 around the image position 516 as a center. Accordingly, segments 520 and 521 are set in correspondence with the cardiac phases 502b and 502c, and view weights 520a and 521a are set with respect to the respective segments. When the cardiac phase 75% is set as a segment position (i), two 75% cardiac phases 503b and 503c exist in the segment range 517 around the image position 516. Accordingly, segments 522 and 523 are set in correspondence with the cardiac phases 503b and 503c, and view weights 522a and 523a are set with respect to the respective segments.

The projection-data selection region calculation unit 209 generates view ranges 524 and 525 necessary for tomographic image generation in the image position 516 by overlaying the segments set in correspondence with the three cardiac phases (25%, 50%, and 75%) (j). The view ranges 524 and 525 show view ranges necessary for tomographic image generation in all the cardiac phases in the image position 516.

Figure 14:
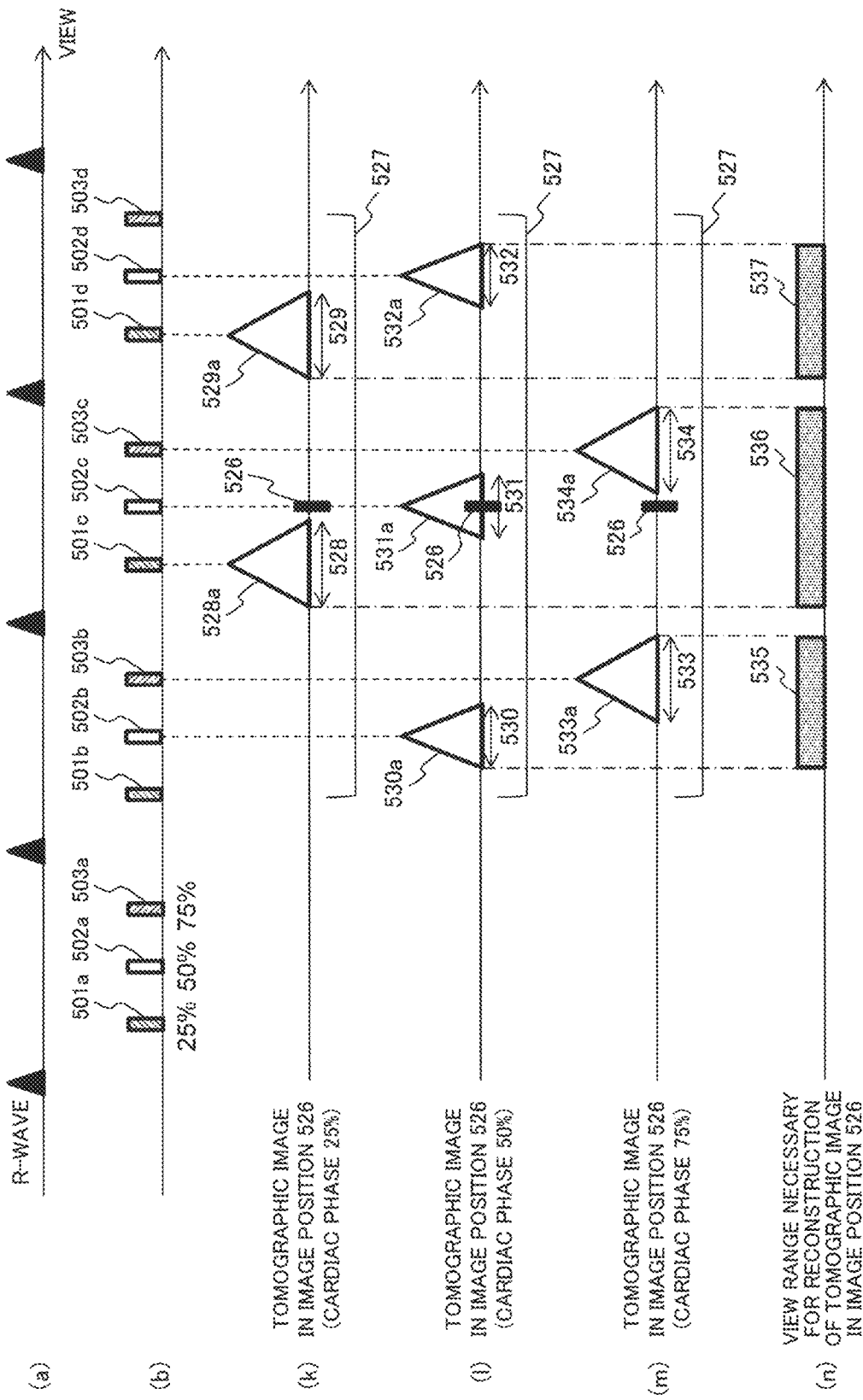
FIG. 14 is a diagram showing view weights for reverse-projecting a tomographic image in a third image position.

FIG. 14 explains a method of calculating a view range necessary for tomographic image generation in an image position 526 different from the image positions 504 and 516. When the cardiac phase 25% is set as a segment position (k), two 25% cardiac phases 501c and 501d exist in a segment range 527 around the image position 526. Accordingly, segments 528 and 529 are set in correspondence with the cardiac phases 501c and 501d, and view weights 528a and 529a are set with respect to the respective segments. When the cardiac phase 50% is set as a segment position (l), three 50% cardiac phases 502b, 502c, and 502d exist in the segment range 527 around the image position 526. Accordingly, segments 530, 531, and 532 are set in correspondence with the cardiac phases 502b, 502c, and 502d, and view weights 530a, 531a, and 532a are set with respect to the respective segments. When the cardiac phase 75% is set as a segment position (m), two 75% cardiac phases 503b and 503c exist in the segment range 527 around the image position 526. Accordingly, segments 533 and 534 are set in correspondence with the cardiac phases 503b and 503c, and view weights 533a and 534a are set with respect to the respective segments.

The projection-data selection region calculation unit 209 generates view ranges 535, 536, and 537 necessary for tomographic image generation in the image position 526 by overlaying the segments set in correspondence with the three cardiac phases (25%, 50%, and 75%) (n). The view ranges 535 to 537 show view ranges necessary for tomographic image generation in all the cardiac phases in the image position 526.

Figure 15:
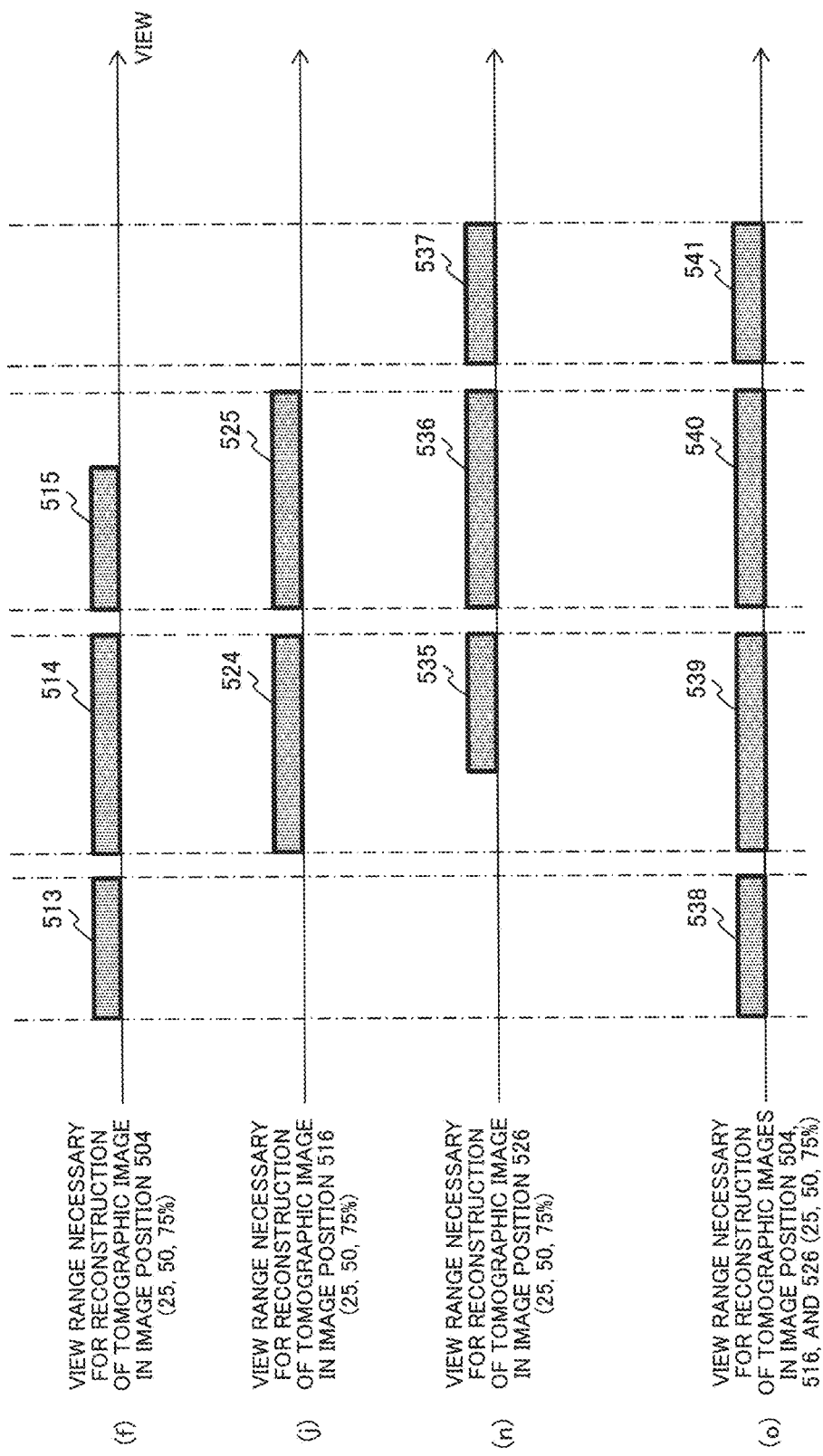
FIG. 15 is a diagram explaining the way of obtaining a view range necessary for reconstruction of the tomographic images in the first to third image positions.

FIG. 15 shows further overlaying of the view ranges 513, 514, 515, 524, 525, 535, 536, and 537 obtained by overlaying the view weights in the three cardiac phases (25%, 50%, and 75%) for tomographic image generation in the respective image positions, with the projection-data selection region calculation unit 209 (o). Since there is no other view range to be overlaid on the view range 513 in the image position 504, as a result, the width of a view range 538 is the same as that of the view range 513. The view range 514 can be overlaid on the view range 524 in the image position 516 and the view range 535 in the image position 526. Note that since the width of the view range 514 and that of the view range 524 are the same, the width of a view range 539 after the overlaying is the same as that of the view range 514 and the view range 524. Similarly, the view range 515 can be overlaid on the view range 525 and the view range 536. Since the width of the view range 525 and that of the view range 536 are the same, the width of a view range 540 after the overlaying is the same as that of the view range 525 and the view range 536. Since there is no other view range to be overlaid on the view range 537 in the image position 526, as a result, the width of a view range 541 is the same as that of the view range 537. The view ranges 538, 539, 540, and 541 thus calculated indicate are view ranges representing regions necessary for tomographic image generation in the three image positions and in the three cardiac phases. Note that in the description of the present example, the tomographic images are generated in the three image positions, although the number of images is not particularly limited. Further, in this example, the view weight is increased and decreased in front and behind the view weight of the projection data in the segment position as a maximum view weight. However, it is not limited to this pattern, and it can be arbitrarily determined in accordance with image sensing conditions.

Figure 16:
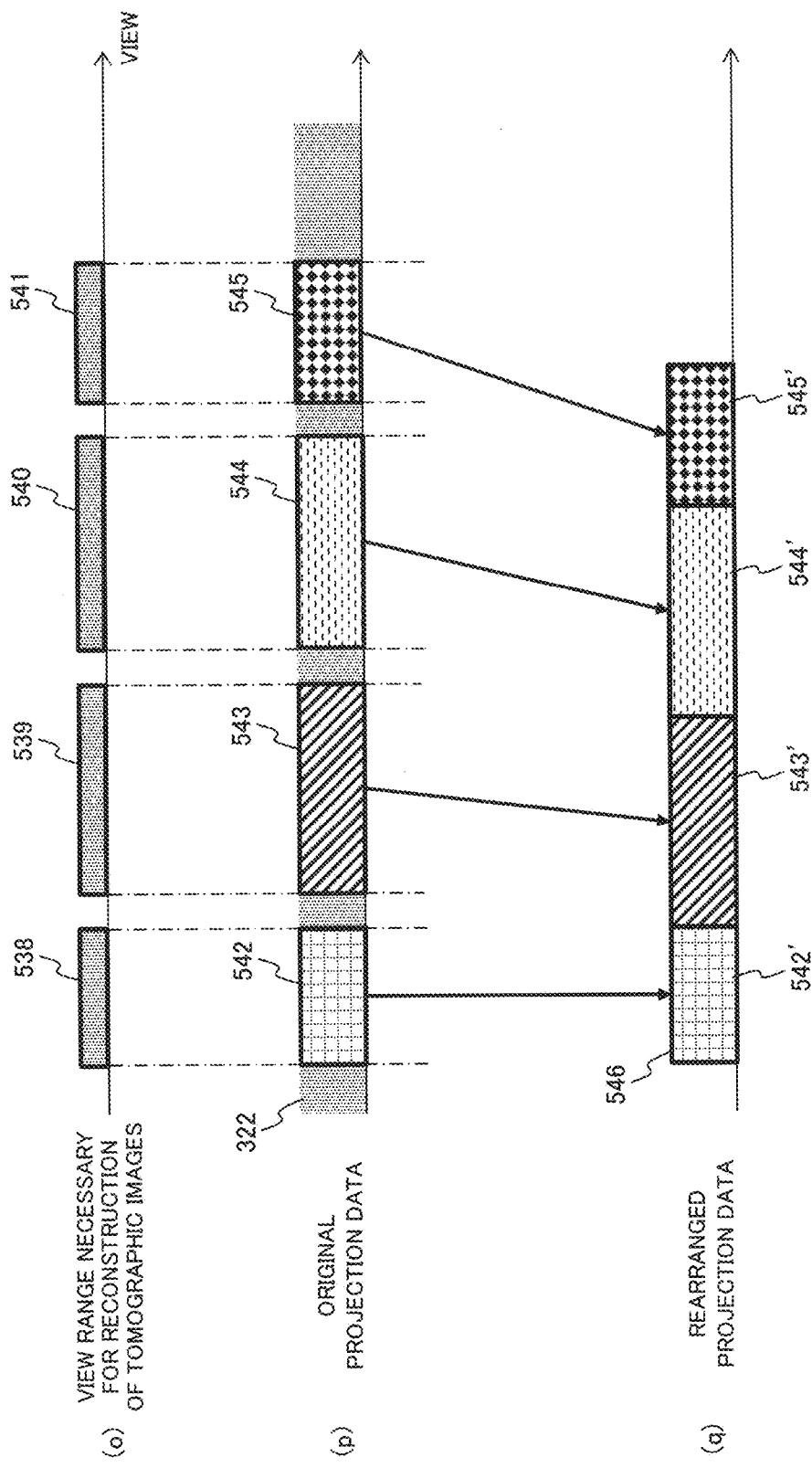
FIG. 16 is a diagram explaining the rearrangement of projection data.

FIG. 16 explains a method of rearranging projection data with the projection-data selection unit 210 based on the selected region described in FIG. 15. The projection-data selection unit 210 reads only protection data necessary for reverse protection from projection data (original projection data) 322 stored in the memory for saving original projection data 205 with the view ranges 533 to 541 calculated with the projection-data selection region calculation unit 209 (p). Then, projection data (rearranged projection data) 546, rearranged by connecting the read projection data, is written into the memory for saving rearranged projection data 212 (q).

Figure 17:
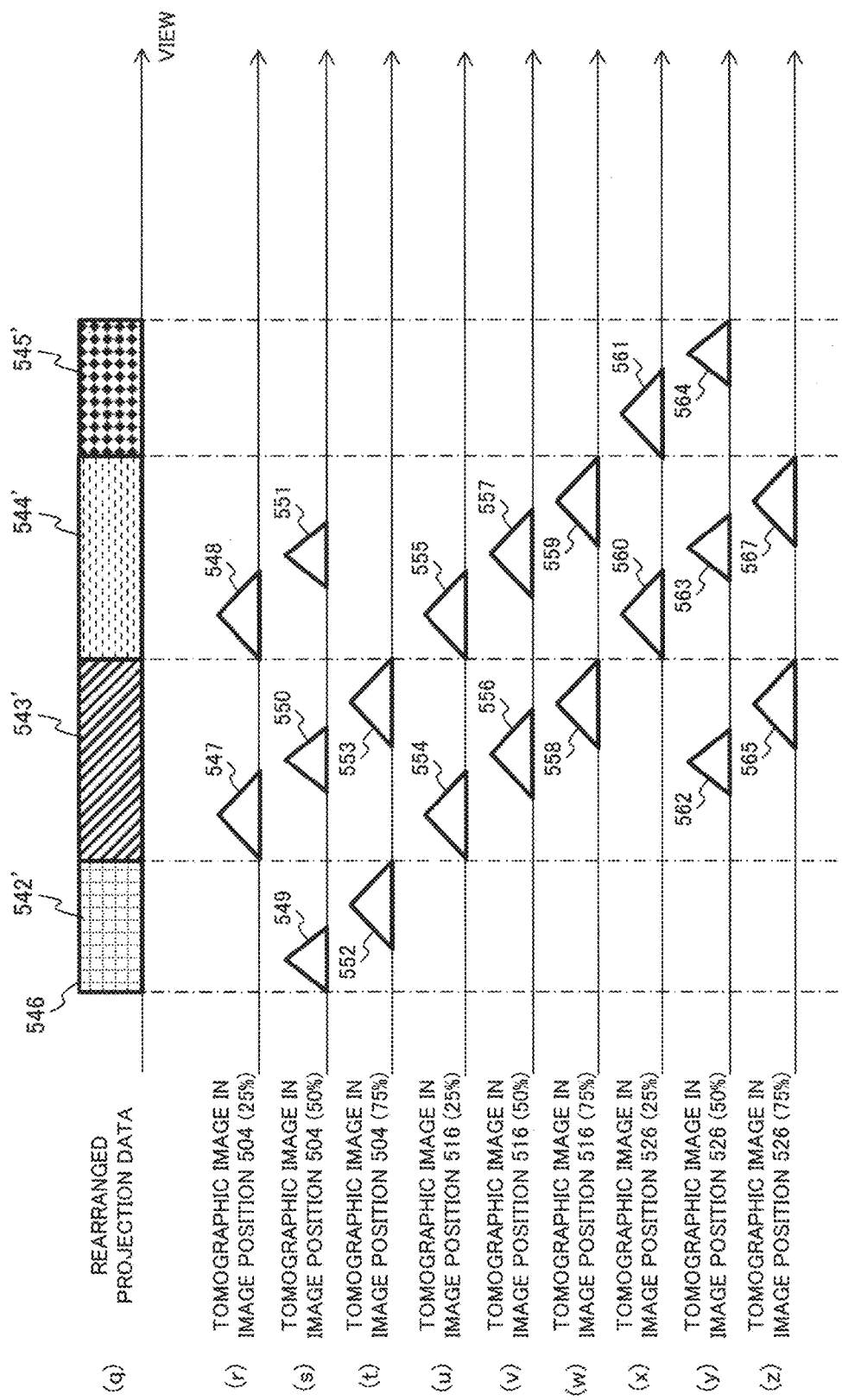
FIG. 17 is a diagram showing view weights in the rearranged projection data.

FIG. 17 explains the details of processing to generate the view weights for the entire image in the respective cardiac phases with respect to the rearranged projection data 546, with the rearranged-projection-data view-weight generation unit 211. The number of segments and the shape of the view weight are the same as those generated with the view-weight generation unit 208 with respect to the initial projection data (original projection data) 322 (see FIGS. 12 to 14), however, as the projection data is rearranged, the position of the view weight is changed.

In the case of a tomographic image in the image position 504 and in the cardiac phase 25% (r), two segments 543' and 544' of the rearranged projection data 546 are used. View weights 547 and 548 are provided such that the left end of the respective view weights is positioned at the left end of the respective segments. In the case of a tomographic image in the image position 504 and in the cardiac phase 50% (s), three segments 542', 543' and 544' of the rearranged projection data 546 are used. The left end of a view weight 549 is positioned at the left end of the segment 542' and view weights 550 and 551 are provided such that the center of the respective view weights is positioned at the center of the segments 543' and 544'. In the case of a tomographic image in the image position 504 and in the cardiac phase 75% (t), two segments 542' and 543' of the rearranged projection data 546 are used. View weights 552 and 553 are provided such that the right end of the respective view weights is positioned at the right end of the respective segments.

In the case of a tomographic image in the image position 516 and in the cardiac phase 25% (u), two segments 543' and 544' of the rearranged projection data 546 are used. View weights 554 and 555 are provided such that the left end of the respective view weights is positioned at the left end of the respective segments. In the case of a tomographic image in the image position 516 and in the cardiac phase 50% (v), the two segments 543' and 544' of the rearranged projection data 546 are used. View weights 556 and 557 are provided such that the center of the respective view weights is positioned at the center of the respective segments. In the case of a tomographic image in the image position 516 and in the cardiac phase 75% (w), the two segments 543' and 544' of the rearranged projection data 546 are used. View weights 558 and 559 are provided such that the right end of the respective view weights is positioned at the right end of the respective segments.

In the case of a tomographic image in the image position 526 and in the cardiac phase 25% (x), two segments 544' and 545' of the rearranged projection data 546 are used. View weights 560 and 561 are provided such that the left end of the respective view weights is positioned at the left end of the respective segments. In the case of a tomographic image in the image position 526 and in the cardiac phase 50% (y), the three segments 543', 544' and 545' of the rearranged projection data 546 are used. The right end of the view weight 564 is positioned at the right end of the segment 545' and view weights 562 and 563 are provided such that the center of the respective view weights is positioned at the center of the segments 543' and 544'. In the case of a tomographic image in the image position 526 and in the cardiac phase 75% (z), the two segments 543' and 544' of the rearranged projection data 546 are used. View weights 565 and 567 are provided such that the right end of the respective view weights is positioned at the right end of the respective segments.

The reverse projection processing unit 214 generates a tomographic image by performing reverse projection processing with the rearranged projection data 546 and view weights 547 to 567 generated in correspondence with the rearranged projection data 546. At this time, since the projection data is always used in the reverse projection processing, the projection data moved from the main memory (memory for saving rearranged projection data 212)

to the cache memory 213 is always used. This improves the cache hit ratio, and leads to reduction of processing time of the reverse projection.

Note that the present example may be used when combined with Example 2.

REFERENCE SIGNS LIST

101: scanner, 102: bed, 103: console, 104: display, 105A: keyboard, 105B: mouse, 106: subject, 107: X-ray tube, 108: X-ray detector, 109: electrocardiographic-waveform acquisition device, 110: X-ray controller, 111: gantry controller, 112: bed controller, 113: detector controller, 114: system controller, 115: image creation unit, 116: image display unit, and 117: operation unit.

The invention claimed is:

1. An X-ray CT apparatus comprising:
an X-ray tube;
an X-ray detector, oppositely provided to the X-ray tube, that detects an X-ray generated with the X-ray tube and transmitted through a subject;
a main memory that stores projection data generated from spatial distribution of the transmission X-ray detected with the X-ray detector;
a cache memory to which the projection data is previously transferred from the main memory; and
a processor that, when the projection data used in reverse projection processing has been transferred to the cache memory, performs the reverse projection processing, with the projection data stored in the cache memory, and generates tomographic image data of the subject,
wherein a first plurality of segments are set based on an image position with respect to original projection data of continuous views from the X-ray detector, and first tomographic image data is generated by reverse-projecting projection data of the first plurality of segments in accordance with first view weights set by the first plurality of segments,
wherein the processor generates rearranged projection data in which the first plurality of segments are extracted from the original projection data, and stores the generated rearranged projection data into the main memory, and generates second view weights, in which the first view weights are made to correspond with the rearranged projection data,
wherein the rearranged projection data stored in the main memory is previously transferred to the cache memory, and
wherein the processor generates the first tomographic image data with the rearranged projection data and the second view weights.

2. The X-ray CT apparatus according to claim 1,
wherein the original projection data is obtained by image sensing with the X-ray tube and the X-ray detector while the X-ray tube and the X-ray detector move in a helix orbital shape around the subject.

3. The X-ray CT apparatus according to claim 2,
wherein the first plurality of segments are set based on a biological signal obtained from the subject.

4. The X-ray CT apparatus according to claim 3,
wherein the biological signal is an electrocardiographic waveform, and the first plurality of segments are set based on a cardiac phase obtained from the electrocardiographic waveform.

5. An X-ray CT apparatus comprising:
an X-ray tube;
an X-ray detector, oppositely provided to the X-ray tube, that detects an X-ray generated with the X-ray tube and transmitted through a subject;
a main memory that stores projection data generated from spatial distribution of the transmission X-ray detected with the X-ray detector;
a cache memory to which the projection data is previously transferred from the main memory; and
a processor that, when the projection data used in reverse projection processing has been transferred to the cache memory, performs the reverse projection processing, with the projection data stored in the cache memory, and generates tomographic image data of the subject,
wherein a first plurality of segments are set based on an image position with respect to original projection data of continuous views from the X-ray detector, and first tomographic image data is generated by reverse-projecting projection data of the first plurality of segments in accordance with first view weights set by the first plurality of segments,
wherein a second plurality of segments are set based on an image position with respect to original projection data, and second tomographic image data is generated by reverse-projecting projection data of the second plurality of segments in accordance with second view weights set by the second plurality of segments,
wherein the processor generates rearranged projection data in which the first plurality of segments and the second plurality of segments are overlaid and extracted from the original projection data and stores the generated rearranged projection data into the main memory, and generates third view weights in which the first view weights are made to correspond with the rearranged projection data, and generates fourth view weights in which the second view weights are made to correspond with the rearranged projection data,
wherein the rearranged projection data stored in the main memory is previously transferred to the cache memory, and
wherein the processor generates the first tomographic image data with the rearranged projection data and the third view weights, and generates the second tomographic image data with the rearranged projection data and the fourth view weights.

6. The X-ray CT apparatus according to claim 5,
wherein the original projection data is obtained by image sensing with the X-ray tube and the X-ray detector while the X-ray tube and the X-ray detector move in a helix orbital shape around the subject.

7. The X-ray CT apparatus according to claim 6,
wherein the first plurality of segments and the second plurality of segments are set based on a biological signal obtained from the subject.

8. The X-ray CT apparatus according to claim 7,
wherein the biological signal is an electrocardiographic waveform, and the first plurality of segments and the second plurality of segments are set based on a cardiac phase obtained from the electrocardiographic waveform.

9. The X-ray CT apparatus according to claim 7,
wherein the image position of the first tomographic image data and the image position of the second tomographic image data are different from each other.

10. The X-ray CT apparatus according to claim 7,
wherein the image position of the first tomographic image data and the image position of the second tomographic image data are the same, and the first plurality of segments and the second plurality of segments are set at different timings with respect to the biological signal.

11. The X-ray CT apparatus according to claim 10, wherein the biological signal is an electrocardiographic waveform, and the first plurality of segments are set based on a first cardiac phase obtained from the electrocardiographic waveform, and the second plurality of segments are set based on a second cardiac phase obtained from the electrocardiographic waveform.

12. The X-ray CT apparatus according to claim 5, wherein the processor divides a view range in correspondence with the number of tomographic images for which respective views included in the rearranged projection data are subjected to reverse projection, and wherein the amount of the rearranged projection data transferred from the main memory to the cache memory is made different in correspondence with the view range.

13. The X-ray CT apparatus according to claim 12, wherein the amount of the rearranged projection data transferred to the cache memory is determined by subtracting the amount of tomographic image data corresponding to the number of tomographic images in the view range from the capacity of the cache memory allocated to the reverse projection processing.

14. The X-ray CT apparatus according to claim 12, wherein the processor is a multi-core processor, and wherein the number of blocks of the tomographic image by block-dividing the tomographic image and located to respective multiple cores is larger than the number of the multiple cores.

* * * * *